United States Patent [19]

Harada et al.

[11] Patent Number: 5,689,040
[45] Date of Patent: Nov. 18, 1997

[54] PLANT PROMOTER SEQUENCES USEFUL FOR GENE EXPRESSION IN SEEDS AND SEEDLINGS

[75] Inventors: John J. Harada, Davis; James Z. Zhang, Palo Alto; Debbie Laudencia-Chingcuanco, Albany, all of Calif.

[73] Assignee: The Regents of the University of California, Oakland, Calif.

[21] Appl. No.: 393,219

[22] Filed: Feb. 23, 1995

[51] Int. Cl.$^6$ .......................... C12N 15/29; C12N 15/82; C12N 15/11; A01H 5/00
[52] U.S. Cl. .................. 800/205; 800/DIG. 15; 536/23.6; 536/24.1; 435/172.3; 435/320.1; 435/419
[58] Field of Search .................. 536/24.1, 23.6; 435/172.3, 240.4, 320.1, 419; 800/205, DIG. 15; 935/35

[56] References Cited

U.S. PATENT DOCUMENTS 5,439,822  8/1995  Katsumata et al. ............ 435/252.32
5,443,974  8/1995  Hitz et al. .................... 435/172.3

OTHER PUBLICATIONS

Graham, Ian A., et al. (1989) "The malate synthase gene of cucumber", *Plant Molecular Biology*, 13:673–684.

Graham, Ian A., et al. (1990) "Developmental regulation of expression of the malate synthase gene in transgenic plants", *Plant Molecular Biology*, 15:539–549.

Graham, Ian A., et al. (1994) "Analysis of the cucumber malate synthase gene promoter by transient expression and gel retardation assays", *The Plant Journal*, 6(6):893–902.

Graham, Ian A., et al. (1992) "Induction of Malate Synthase Gene Expression in Senescent and Detached Organs of Cucumber", *The Plant Cell*, 4:349–357.

Graham, Ian A., et al. (1994) "Carbon Catabolite Repression Regulates Glyoxylate Cycle Gene Expression in Cucumber", *The Plant Cell*, 6:761–772.

Reynolds, Susan J., et al. (1995) "The isocitrate lyase gene of cucumber:Isolation, characterisation and expression in cotyledons following seed germination", *Plant Molecular Biology*, 27:487–497.

Comai, Lucio, et al. (1989) "Deduced Sequence of a Malate Synthase Polypeptide Encoded by a Subclass of the Gene Family", *The Journal of Biological Chemistry*, 264(5):2778–2782.

Comai, Lucio, et al. (1992) "Expression of a *Brassica napus* Malate Synthase Gene in Transgenic Tomato Plants during the Transition from Late Embryogeny to Germination", *Plant Physiol.*, 98:53–61.

Leyva, Antonio, et al. (1992) "cis–Element Combinations Determine Phenylalanine Ammonia–Lyase Gene Tissue–Specific Expression Patterns", *The Plant Cell*, 4:263–271.

Benfy, Philip N., et al. (1990) "Sequence Requirements of the 5–Enolpyruvylshikimate–3–phosphate Synthase 5'–Upstream Region for Tissue–Specific Expression in Flowers and Seedlings", *The Plant Cell*, 2:849–856.

Zhang, James J., et al. (1993) "Two classes of isocitrate lyase genes are expressed during late embryogeny and postgermination in *Brassica napus* L.", *Mol Gen Genet*, 238:177–184.

Zhang, James Z., et al. (1994) "Isocitrate Lyase and Malate Synthase Genes from *Brassica napus* L. Are Active in Pollen", *Plant Physiol.*, 104:857–864.

Bevan, Michael, et al. (1989) "Tissue—and cell–specific activity of a phenylalanine ammonia–lyase promoter in transgenic plants", *The EMBO Journal*, 8(7):1899–1906.

Benfey, Philip N., et al. (1990) "Combinatorial and synergistic properties of CaMV 35S enhancer subdomains", *The EMBO Journal*, 9(6):1685–1696.

Bowyer et al 1994 (Feb.) Mol Gen Genet 242:484–489.

Scholer et al. 1994 (Jun.) Mol and Cell Biol 14(6):3613–3622.

Scholer et al 1993 Current Genetics 23:375–381.

Fernandez et al. 1993 FEBS Letters 333 (3):238–242.

Comai et al. 1989 The Plant Cell 1:293–300.

*Primary Examiner*—David T. Fox
*Assistant Examiner*—Thomas Haas
*Attorney, Agent, or Firm*—Townsend and Townsend and Crew

[57] ABSTRACT

This invention relates to compositions and methods useful in the production of transgenic plants. In particular, the invention relates to malate synthase and isocitrate lyase plant promoter sequences which are useful for directing expression of heterologous DNAs in seeds and seedlings. The invention also relates to expression cassettes containing the promoter sequences and to transgenic plants containing the expression cassettes.

19 Claims, 9 Drawing Sheets

```
-170                                              -1
    GATA  GATA GATA              TATA
```
|   | MS-A | -123 | ACGAAAAGCATACATAAC | -106 |
|---|------|------|--------------------|------|
|   |      |      | ‖‖‖‖‖‖‖‖ ‖‖ ‖‖‖‖‖ |      |
|   | ILA  | -1708| ACGAAAAGATTATATAAC | -1691|
FIG. 2A.
FIG. 2B.
|   | MS-A | -77  | ATCTCAGGCA | -68  |
|---|------|------|------------|------|
|   |      |      | ‖‖‖‖ ‖‖‖‖‖ |      |
|   | ILA  | -355 | ATCTTAGGCA | -346 |
FIG. 2C.
FIG. 2D.

| Construct | PARTICLE GUN | TRANSPONICE |
|---|---|---|
| -3500 —[GUS] | YES | YES |
| -2700 —[GUS] | YES | YES |
| -2700Δ(1200-590) —[GUS] | | YES |
| -2700Δ(590-350) —[GUS] | | YES |
| -2700Δ(350-30) —[GUS] | | YES |
| -2700Δ(1200-30) —[GUS] | | YES |
| -1700 —[GUS] | YES | YES |
| -1200 —[GUS] | YES | YES |
| -812 —[GUS] | YES | |
| -590 —[GUS] | YES | YES |
| -390 —[GUS] | YES | |
| -350 —[GUS] | YES | YES |
| -329 —[GUS] | YES | |
| -80 —[GUS] | YES | |
| -30 —[GUS] | YES | YES |
| -(590-350)MP —[GUS] | YES | YES |

*FIG. 7.*

PLANT PROMOTER SEQUENCES USEFUL FOR GENE EXPRESSION IN SEEDS AND SEEDLINGS

This invention was made with Government support under Grant No. DCB-8819315, DCB-9118120, and IBN-9317526, awarded by the National Science Foundation. The Government has certain rights in this invention.

BACKGROUND OF THE INVENTION

The present invention relates to plant molecular biology. In particular, it relates to promoter sequences useful for gene expression in selected plant organs and tissues.

Isolated plant promoters are useful in the genetic engineering of plants to produce transgenic plants with desired phenotypes. To produce such transgenic plants, an isolated plant promoter is inserted into a vector and operably linked to a heterologous DNA sequence. Plant cells are then transformed with the vector such that expression of the heterologous DNA is controlled by the promoter.

Generally, plant promoters may be tissue-specific or may constitutive and drive expression in essentially all tissues and organs. Tissue-specific promoters may also be inducible, e.g., by application of external inducing agents, such as light. Tissue-specific or inducible promoters can be identified from genes which are expressed in particular tissues or at particular times during development. For example, isocitrate lyase and malate synthase are enzymes whose expression is developmentally regulated. These enzymes are part of the glyoxylate cycle, a pathway responsible for the net conversion of two molecules of acetyl coenzyme A into succinate (Trelease, el. al., *Seed Physiology*, Vol 2 *Germination and Reserve Mobilization*, D. R. Murray (Ed.), Academic Press, Australia, pp. 202–245 (1984)).

Isocitrate lyase enzyme activities, protein and mRNA are present in seedlings and are not detected in non-senescing leaves of the mature plant. However, the enzyme and mRNA are initially detected in late stage embryos. Although isocitrate lyase is encoded by a multigene family, the same isocitrate lyase gene is activated in both seeds and seedings (Zhang, et al., *Mol. Gen. Genet.* 238:177–184 (1993)).

Malate synthase in *Brassica napus* is encoded by a small gene family Comai et al. *J. Biol Chem* 264:2778-2782 (1989). Analysis of the expression of the different malate synthase gene shows that one class, MS-A, is highly expressed both in seedling and seeds (Comai, et al., *Plant Physiol.* 98:53–61 (1992)). Although accumulation of malate synthase mRNA is modulated by post-transcriptional and post-translational processes, the gene is primarily regulated at the level of transcription.

As noted above, a need exists for a variety of different promoters to be used in the genetic engineering of plants. New tissue-specific promoters are particular useful for the controlled expression of various nucleic acid sequences in transgenic plants. The present invention addresses these and other needs.

SUMMARY OF THE INVENTION

The present invention provides expression cassettes comprising a malate synthase promoter or an isocitrate lyase promoter operably linked to a heterologous nucleic acid sequence. The promoters provide tissue specific expression of the heterologous sequences. In particular, the promoters are useful in expression in seeds and seedlings. The promoter is typically derived from member of the genus Brassica. An exemplary malate synthase promoter is shown in SEQ ID NO: 1. An exemplary isocitrate lyase promoter is shown in SEQ ID NO: 2.

To ensure tissue-specific expression of the operably linked heterologous nucleic acid sequence, the promoter may comprise a sequence extending from about −2700 to about −1700, from about −1700 to about −590, or from about −590 to about −350 of a isocitrate lyase promoter. In other embodiments, the promoter comprises a sequence extending from about −170 to about −32 of a malate synthase promoter.

The invention also provides transgenic plant comprising the expression cassettes described above. The plant may be a member of the Brassica family or other agronomically useful plant.

The invention further provides methods of expressing a heterologous nucleic acid sequence in a plant. The methods comprise introducing into plant tissue a vector comprising the expression cassette described above and regenerating the plant tissue into a whole plant.

DEFINITIONS

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. Sequence regions on a DNA strand which are 5' to the 5' end of an RNA transcript encoded by the DNA are referred to as "upstream sequences". Upstream sequences are usually counted in a negative direction from the transcription start site. In the sequences disclosed here, the transcription start site is located at nucleotide 1753 in SEQ ID No: 1 and nucleotide 2802 in SEQ ID NO: 2. Sequence regions on the DNA strand which are 3' to the 3' end of the RNA transcript are referred to as "downstream sequences".

The term "promoter" refers to a region of DNA upstream from the translational start codon and which is involved in recognition and binding of RNA polymerase and other proteins to initiate transcription. A "plant promoter" is a promoter capable of initiating transcription in plant cells. The terms "isocitrate lyase promoter" or "malate synthase promoter" as used herein refer to plant promoters comprising sequences derived from the promoter region of these genes, respectively. The promoters of the invention preferably contain tissue specific elements identified here, that allow tissue specific transcription of operably linked DNA sequences. The promoters are considered to be tissue-specific promoters because transcription of the operably linked DNA is higher in one or more plant tissues than it is in other tissues. In particular, the promoters of the invention selectively express operably linked DNA sequences in seedlings or seeds.

A "tissue-specific" promoter as used herein refers to a promoter that drives expression of an operably linked nucleic acid sequence in a particular tissue in a plant or at a particular stage in the plant life-cycle.

The term "operably linked" as used herein refers to linkage of a promoter upstream from a DNA sequence such that the promoter mediates transcription of the DNA sequence. It is understood that the promoter sequence aim includes transcribed sequences between the transcriptional start and the translational start codon.

The phrase "expression cassette", refers to nucleotide sequences which are capable of affecting expression of a structural gene in hosts compatible with such sequences.

Such cassettes include at least promoters and optionally, transcription termination signals. Additional factors necessary or helpful in effecting expression may also be used as described herein.

A "heterologous" nucleic acid or protein is one that originates from a foreign source (or species) or, if from the same source, is modified from its original form. Thus, a heterologous promoter sequence in an expression cassette is from a source different from that from which encoding sequence was derived, or, if from the same source, is modified from its original form. Modification may occur, e.g., by treating the DNA with a restriction enzyme to generate a promoter element that is capable of conferring tissue-specific expression on the expression cassette which includes it.

The phrases "isolated" or "substantially pure" when referring to a polynucleotide or protein, means a chemical composition which is free of other subcellular components of the organism from which it is derived, e.g., Brassica plants. Typically, a compound is substantially pure when at least about 85% or more of a sample exhibits a single polypeptide backbone, or polynucleotide sequence. Minor variants or chemical modifications may typically share the same polypeptide sequence. Depending on the purification procedure, purities of 85%, and preferably over 95% pure are possible. Nucleic acid and protein purity or homogeneity may be indicated by a number of means well known in the art, such as gel electrophoresis and the like.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous and dicotyledonous plants.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis, or BlastN and BlastX available from the National Center for Biotechnology Information), or by inspection. Sequences are typically compared using BESTFIT or BlastN with default parameters.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Polypeptides which are "substantially similar" share sequences as noted above except that residue positions which are not identical may differ by conservative amino acid changes. Conservative amino acid substitutions refer to the interchangeability of residues having similar side chains.

Another indication that polynucleotide sequences are substantially identical is if two molecules selectively hybridize to each other under stringent conditions. The phrase "selectively hybridizing to" refers to a nucleic acid probe that hybridizes or binds only to a particular target DNA or RNA sequence when the target sequences are present in a preparation of total cellular DNA or RNA. Stringent conditions are sequence dependent and will be different in different circumstances. Generally, stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe.

BRIEF DESCRIPTION OF THE DRAWINGS

FIGS. 2A–2D shows conserved DNA sequences in the promoters of malate synthase and isocitrate lyase genes.

FIG. 6C shows the ratio of activity in light and dark grown seedlings.

FIG. 7 is a diagrammatic representation of the chimeric constructs used for expression of the isocitrate lyase promoter fused to the GUS gene.

FIG. 9A shows activity in seed; FIG. 9B shows activity in seedling; and FIG. 9C shows activity in leaf.

DESCRIPTION OF THE PREFERRED EMBODIMENT

Figure 1A:
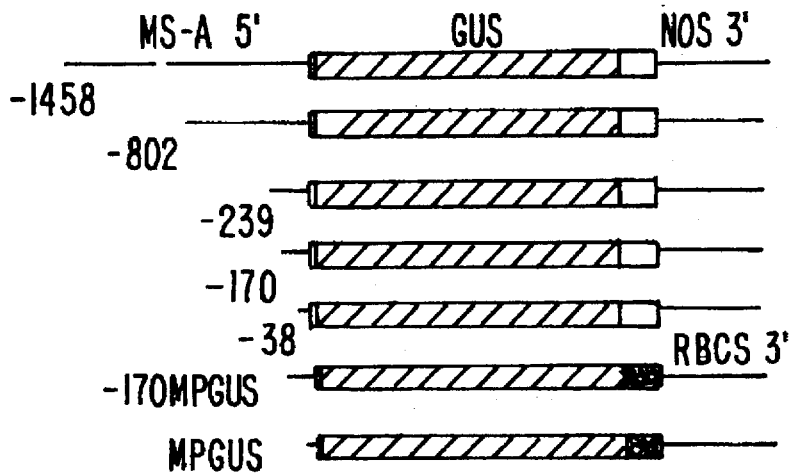
FIG. 1A is a diagrammatic representation of the chimeric constructs used for transient expression of the malate synthase promoter fused to the GUS gene in Brassica napus seedlings and leaves.

The present invention provides new plant promoter sequences useful for expression of desired nucleic acid sequences in seeds and seedlings. In particular, the invention provides isolated nucleic acid molecules comprising sequences from promoters derived from isocitrate lyase and malate synthase genes, which are active primarily during seed development. The present invention provides cis-acting elements that play a role in the activation of gene expression in seedling development, but have little or no effect on the expression of the genes in other organs. Thus the promoter sequences of the invention can be used to drive expression of a variety of heterologous nucleic acids sequences in seedlings and seeds of transgenic plants.

I. Isolation of Isocitrate Lyase and Malate Synthase Promoters

The promoter sequences of the invention are typically identical to or show substantial sequence identity (determined as described above) to portions of the malate synthase promoter nucleotide sequence depicted in SEQ ID NO: 1 or the isocitrate lyase promoter nucleotide sequence depicted in SEQ ID NO: 2. A number of different promoters having homology or substantial sequence identity to the promoter sequences of SEQ ID NO: 1 and SEQ ID NO: 2 may be isolated from members of the Brassica family, such as Brassica or Arabidopsis.

Malate synthase promoter sequences typically hybridize to the nucleic acids having a sequence as shown in SEQ ID NO: 1 under stringent conditions. Isocitrate lyase promoters typically hybridize to SEQ ID NO: 2 under stringent conditions. Typically stringent conditions for a Southern blot protocol involve washing at 55° C. with 0.2XSSC.

There are a variety of methods that may be used for isolation of isocitrate lyase or malate synthase promoter sequences. For example, DNA can be isolated from a genomic library using labelled nucleic acid probes having sequences complementary to the sequences disclosed here. Full-length probes may be used, or oligonucleotide probes may also be generated. Alternatively, genomic clones comprising the genes can be isolated and the 5' end of the clones can be subcloned to provide the promoter sequences. Techniques for nucleic acid manipulation of genes such as subcloning nucleic acid sequences encoding polypeptides into expression vectors, labelling probes, DNA hybridization, and the like are described generally in Sambrook, et al., *Molecular Cloning—A Laboratory Manual* (2nd Ed.), Vol. 1–3, Cold Spring Harbor Laboratory, Cold Spring Harbor, N.Y. (1989). This manual is hereinafter referred to as "Sambrook, et al."

In addition to screening using the sequences disclosed here, techniques designed to identify sequences specific to a particular tissue or cell types can be used to isolate sequences of the invention (see, e.g., Sambrook, et al.) Such techniques include differential hybridization techniques as described in the example section or in Gurr, et al. *Mol. Gen. Genet.* 226:361–366 (1991). In addition, subtractive hybridization techniques can be used to prepare specific probes for screening cDNA or genomic libraries. These techniques can also be used to prepare subtracted libraries enriched for the desired sequences. Once a desired genomic clone is identified, the 5' sequences can be analyzed to identify the promoter sequence from the gene. This can be accomplished using deletion analysis and a promoterless reporter gene (e.g., GUS) to identify those regions which can drive expression of a structural gene.

Nucleic acid amplification techniques such as polymerase chain reaction (PCR) technology, can also be used to amplify the desired genes and promoter sequences from mRNA, from cDNA, and from genomic libraries or cDNA libraries. In PCR techniques, oligonucleotide primers based on the sequences disclosed here and complementary to the two 5' and 3' borders of the DNA region to be amplified are synthesized. The polymerase chain reaction is then carried out using the two primers. See PCR *Protocols: A Guide to Methods and Applications* (Innis, M, Gelfand, D., Sninsky, J. and White, T., eds.), Academic Press, San Diego (1990). Primers can be selected to amplify the entire regions encoding a full-length isocitrate lyase or its promoter. PCR can also be used to amplify smaller DNA segments of these regions as desired.

Oligonucleotides for use as primer or probes in the above-mentioned procedures can be chemically synthesized according to standard techniques such as the solid phase phosphoramidite triester method first described by Beaucage, et al., *Tetrahedron Lett.* 22(20): 1859–1862 (1981), using an automated synthesizer, as described in Needham-VanDevanter, et al, *Nucleic Acids Res.* 12:6159–6168 (1984).

As demonstrated below, different forms of the promoters of the invention can be produced that have different properties. For example, sequences from the isocitrate lyase and malate synthase promoters which comprise positive elements for expression in seeds and/or seedlings can be used to direct expression of heterologous nucleic acids in these organs. Thus, promoter sequences comprising the sequences identified here are particularly useful in driving specific expression of heterologous sequences in seedlings and seeds.

Typically, the malate synthase promoters of the invention will be about 170 nucleotides to about 1800 nucleotides in length, usually between about 200 to about 1500 nucleotides. Isocitrate lyase promoters of the invention will typically be 1200 to about 3500 nucleotides in length, usually between about 1700 to about 2700 nucleotides.

As demonstrated below, sequences which confer tissue specific expression are found in the promoters of the invention. Thus, heterologous promoters can be constructed which have tissue specific expression as a result of the presence of tissue specific elements contained in these sequences. For instance, seedling specific elements are identified in the malate synthase gene between about −170 and −32. In addition, sequences between −107 to −54 are important for expression in seedlings. In the isocitrate lyase promoter, sequences which confer seedling and seed specific expression are found from about −2700 to about −1700, from about −1700 to about −1200, and from about −1200 to about −590. Seed specific elements are located from about −3000 to about −2700, about −1700 to about −1200, and about −590 to about −390.

II. Construction of Expression Cassettes and Vectors

The methods required for construction of vectors containing expression cassettes comprising a promoter of the invention operably linked to desired sequence are well known.

The minimal requirements of the vector are that the desired nucleic acid sequence be introduced in a relatively intact state. Thus, any vector which will produce a plant carrying the introduced DNA sequence should be sufficient. The selection of vectors and methods to construct them are commonly known to persons of ordinary skill in the art and are described in general technical references (See, in general, *Methods in Enzymology* Vol. 153 ("Recombinant DNA Part D") 1987, Wu and Grossman Eds., Academic Press.

The recombinant vectors of the present invention typically comprise an expression cassette designed for initiating transcription of the desired polynucleotide sequences in plants. Companion sequences, of bacterial origin, are also included to allow the vector to be cloned in a bacterial host. The vector will preferably contain a broad host range prokaryote origin of replication. A selectable marker should also be included to allow selection of bacterial cells bearing the desired construct. Suitable prokaryotic selectable markers include resistance to antibiotics such as kanamycin or tetracycline.

For expression of polypeptides in plants, the recombinant expression cassette will contain, in addition to the desired polynucleotide sequence and the promoter sequence of the invention, a translation initiation site (if the sequence to be transcribed lacks one), and a transcription termination sequence. Unique restriction enzyme sites at the 5' and 3 ' ends of the cassette are typically included to allow for easy insertion into a preexisting vector.

In the construction of heterologous promoter/structural gene combinations, the promoter is preferably positioned about the same distance from the heterologous transcription start site as it is from the transcription start site in its natural setting. As is known in the art, however, some variations in this can be accommodated without loss of promoter function.

As noted above, an expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419–434, 1982. Polyadenylation sequences include, but are not limited to the Agrobacterium octopine synthase signal (Gielen et at., *EMBO J.*, 3:835–846, 1984) or the nopaline synthase signal (Depicker et at., *Mol. and Appl. Genet*, 1:561–573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

Examples of suitable structural genes that can be expressed using the promoter sequences of the invention include genes for herbicide resistance; genes for fungal disease resistance (e.g., chitinases and glucanases); genes for bacterial disease resistance (e.g., cecropins); and genes for insect resistance (e.g., *B. thuringiensis* toxin).

DNA constructs containing a malate synthase or an isocitrate lyase promoter can be used in techniques to suppress expression of endogenous plant genes. Examples of such techniques include antisense suppression, sense suppression and ribozymes.

In antisense technology, a nucleic acid segment from the desired plant gene is cloned and operably linked to the promoter sequence such that the anti-sense strand of RNA will be transcribed. The construct is then transformed into plants and the anti-sense strand of RNA is produced. In plant cells, it has been shown that anti-sense RNA inhibits gene expression; see, e.g., Sheehy et al., *Proc. Nat. Acad. Sci. USA* 85:8805–8809 (1988), and Hiatt, et al., U.S. Pat. No. 4,801,340.

The nucleic acid segment to be introduced in antisense suppression generally will be substantially identical to at least a portion of the endogenous gene or gene to be repressed, but need not be identical. The vectors can thus be designed such that the inhibitory effect applies to other proteins within a family of genes exhibiting homology or substantial homology to the target gene. The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective.

Introduction of a nucleic acid configured in the sense orientation has also been shown to be an effective means by which to block the transcription of target genes. For examples of the use of sense suppression to modulate expression of endogenous genes see, Napoli, et al., *The Plant Cell* 2:279–289 (1990), and U.S. Pat. No. 5,034,323. As in antisense suppression, the introduced sequence may be a fragment of the endogenous sequence intended to be repressed and need not be identical to it.

Catalytic RNA molecules or ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature*, 334:585–591 (1988).

Expression of a number of genes can be suppressed using the techniques described above. For example, genes involved in shoot development (e.g., shoot meristemless), root development (e.g., cobra, lion's tail, and sabre) or those involved in providing nutrients for the seedling (e.g., proteases, lipases, and glyoxylate cycle enzymes).

III Production of Transgenic Plants

Techniques for transforming a wide variety of higher plant species are well known and described in the literature. See, for example, Weising, et al., *Ann. Rev. Genet.* 22:421–477 (1988). DNA constructs containing the promoter sequenced linked to heterologous DNA can be introduced into the genome of the desired plant host by a variety of conventional techniques. For example, the DNA construct may be introduced directly into the genomic DNA of the plant cell using techniques such as electroporation and microinjection of plant cell protoplasts. Alternatively, the DNA constructs can be introduced directly to plant tissue using ballistic methods, such as DNA particle bombardment. Usually, the DNA constructs are combined with suitable T-DNA flanking regions and introduced into a conventional *Agrobacterium tumefaciens* host vector.

Direct transformation techniques are known in the art and well described in the scientific literature. The introduction of DNA constructs using polyethylene glycol precipitation is described in Paszkowski, et al., *Embo. J.* 3:2717–2722 (1984). Electroporation techniques are described in Fromm, et al., *Proc. Natl. Acad. Sci. USA* 82:5824 (1985). Ballistic transformation techniques are described in Klein, et al., *Nature* 327:70–73 (1987).

Agrobacterium-meditated transformation techniques are the most commonly used techniques and are well described in the scientific literature. See, for example Horsch, et al. *Science* 233:496498 (1984), and Fraley, et al., *Proc. Natl. Acad. Sci. USA* 80:4803 (1983).

The expression of the heterologous DNA sequences can be detected in a variety of ways, depending on the nature of heterologous sequences. For instance, resistance to an herbicide or pathogen can be detected by treatment with the herbicide or pathogen. Expression can aim be detected by measurement of the specific RNA transcription product. This can be done by, for example, Northern blot procedures. If heterologous DNA sequences encode a novel protein, the protein product may be assayed, for instance, by its function or by a variety of immunoassay techniques.

Transformed plant cells which are derived by any of the above transformation techniques can be cultured to regenerate a whole plant which possesses the desired transformed phenotype. Plant regeneration from cultured protoplasts is described in Evans, et al., *Protoplasts Isolation and Culture, Handbook of Plant Cell Culture*, MacMillan Publishing Company, New York, pp. 124–176 (1983); and Binding, *Regeneration of Plants, Plant Protoplasts*, CRC Press, Boca Raton, pp. 21–73 (1985). Regeneration can also be obtained from plant callus, explants, organs, or parts thereof. Such regeneration techniques are described generally in Klee, et al., *Ann. Rev. of Plant Phys.* 38:467–486 (1987).

One of skill will recognize that, after an expression cassette comprising a malate synthase or isocitrate lyase promoter sequence is stably incorporated in transgenic plants and confirmed to be operable, it can be introduced into other plants by sexual crossing. Any of a number of standard breeding techniques can be used, depending upon the species to be crossed.

The promoter sequences of the invention can be used in the transformation of any plant, including both dicots and monocots. Transformation of dicots is described in references above. Transformation of monocots is known using various techniques including electroporation (e.g., Shimamoto, et al., *Nature* 338:274–276 (1992); ballistics (e.g., European Patent Application 270,356); and Agrobacterium (e.g., Bytebier, et al., *Proc. Natl. Acad. Sci. USA* 84:5345–5349 (1987)).

The methods and compositions of the invention have use over a broad range of types of plants, including species from the genera Fragaria, Lotus, Medicago, Onobrychis, Trifolium, Trigonella, Vigna, Citrus, Linum, Geranium, Manihot, Daucus, Arabidopis, Brassica, Raphanus, Sinapis, Atropa, Capsicum, Hyoscyumus, Lycopersicon, Nicotiana, Solanum, Petunia, Digitalis, Majorana, Ciohorium, Helianthus, Lactuca, Bromus, Asparagus, Antirrhinum, Herecocallis, Nemesia, Pelargonium, Panicum, Pennisetum, Ranunculus, Senecio, Salpiglossis, Cucumis, Browaalia, Glycine, Lolium, Zea, Triticum, Sorghum, Datura, Chrysanthemum, Dianthus, Gerbera, Euphorbia, Ipomoea, Passiflora, Cyclamen, Malus, Prunus, Rosa, Rubus, Populus, Santalum, Allium, Lilium, Narcissus, Ananas, Arachis, Phaseolus and Pisum. Of particular interest are plants in the Brassica family such as broccoli, cauliflower, and related crucifers (Brassica sp.), and oil crops such as canola (Brassica sp.).

The following examples are provided by way of illustration and not limitation.

EXAMPLE 1

Analysis of Malate Synthase Promoter Sequences

Particle gun-mediated gene transfer and stable plant transformation were used to delineate sequence elements that activate the malate synthase promoter in various tissues. In particular, a series of deletions in the promoter was generated to localize the DNA sequences required for expression.

I. Particle Gun-Mediated Gene Transfer

A. Materials and Methods

1. Plant Material

*Brassica napus* L. (rapid cycling base population, CrGC5) seeds were grown in moist vermiculite and UC modified mix for 14 days under standard greenhouse conditions. The first and second sets of leaves from these two-week old plants were used for the experiments. Two-day old etiolated seedlings were from surface sterilized seeds grown at 25 C in half-strength MSO agar plates in the dark (2.2 g/L of Murashige and Skoog salts, 50 µg/ml myo-inositol, 0.5 µg/ml thiamine-HCl, 0.25 µg/ml nicotinic acid, 0.25 µg/ml pyrodixine-HCl, 8 g bacto agar/L).

2. Plasmid Construction

An 8.4 kb XhoI fragment containing the *Brassica napus* MS-A gene coding for malate synthase was excised from clone MS 12 (Comai, et al., *Plant Physiol.* 98:53–61 (1992)) and 5' terminal deletion derivatives generated by Exonuclease III digestion were ligated into pUC129. The 5' deletion derivatives in pUC129 were digested with PflMI, which conveniently cuts 5' of the first nucleotide of the translated ATG codon, blunt-ended, digested with SstI and ligated into a pBluescript II KS +/—(Stratagene) cassette plasmid containing a β-glucuronidase gene protein coding region (GUS) fused with a nopaline synthase (NOS) 3' terminator (Depicker, et al., *J. Mol. Appl. Genet.* 1:561–573 (1982)). 5' deletion derivatives of the malate synthase upstream region fused to GUS/NOS were designated MSGUS. The junctions of the chimeric fusions were verified by DNA sequencing.

To generate the gain-of-function construct, DNA sequences at −170 to −32 region of the malate synthase upstream region were amplified. The primer pair of a 24-mer forward primer 5'-GACGTTGTAAAACGACGGCCAGTG-3' (SEQ ID NO: 3) for pBluescript II KS +/—(Stratagene) and a 39-mer primer, 5'TCAGAGCTFCGGATCCGGTGGAAATGGATA GGGGATATGC-3' (SEQ ID NO: 4) (−33 and −56 of the malate synthase upstream region, plus a 15 bp adapter for BamHI and SstI) was used for PCR reactions. PCR-amplified fragments were subcloned into a construct containing the CaNV35S minimal promoter (−46/+8) fused to a GUS coding region with the terminator from a ribulose-1, 5-hisphosphate carboxylase/oxygenase small (RBCS) subunit gene (Benfey, et al., *Embo. J.* 9:1685–1696 (1990)). The sequence of the subcloned PCR-amplified fragment was verified using the M13 universal primer and a 30-met primer complementary to the 5' end of the protein coding region of GUS gene.

The constructs used in the experiments are illustrated in FIG. 1A. MS-A 5' refers to 1458 to +31 upstream region of *B. napus* MS-A malate synthase gene; GUS, protein coding region of the bacterial β-glucuronidase gene (uiaD); NOS 3', nopaline synthase II gene 3' terminator region. MPGUS refers to the minimal promoter of cauliflower mosaic virus 35S gene (CaMV35S) from positions −46 to +8 relative to the transcription start site fused to GUS with the terminator region from a rubisco small subunit gene (RBCS 3'). The number preceding each construct refers to the 5' terminal end of the gene from the transcription start site. The constructs are referred to below as −145BMSGUS, −802MSGUS, −239MSGUS, −170MSGUS, −38MSGUS, −170MPGUS and MPGUS.

To normalize for variations in the efficiency of the delivery of DNA into the tissues between each bombardment, promoter activity of the indicated chimeric construct is reported as a ratio of GUS activity relative to the activity of luciferase (LUC) internal control. A firefly luciferase gene fused with the CaMV35S promoter (CaMV35SLUC, pAH18) was used (Bruce, et al., *Embo. J.* 10:3015–3024 (1991)). The GUS gene was fused to the CaMV35S promoter (CaMV35SGUS) as a positive control.

3. Transient Assays

The particle delivery system from Bio-Rad (Biolistic PDS 1000) was used to introduce DNA into the tissue of interest. Precipitation of DNA onto microprojectiles and bombardment were carded out as described by Klein, et al., *Bio/Technology* 6:559–563 (1988); Klein, et al., *Proc. Natl. Acad. Sci. USA* 86:6681–6685 (1989).

The first and second set of leaves from 14 day old *Brassica napus* plants grown in the greenhouse were harvested. Leaves that are about 2–3 cm in length were surface-sterilized with 2% Chlorox, 0.05% Tween 80 for 15–20 min, rinsed three times with sterile distilled water and placed adaxial-side up onto sterile, half-strength MSO agar plates. The leaves were either used on the same day or incubated overnight at 25° C. under 16 hour light period before bombardment.

Cotyledon pairs from two day old seedlings of *B. napus* were harvested immediately prior to bombardment. Ten pairs of cotyledons were separated from the axis and transferred to fresh half-strength MSO agar plates.

The bombarded tissue was incubated at 25° C. overnight either in the dark (for cotyledons) or in the light (for leaves) before proteins were extracted and assayed for GUS and luciferase (LUC) activities.

4. Enzyme assays

Proteins were extracted from bombarded seedlings or leaves in 0.5 ml GUS extraction buffer (0.2M sodium phosphate, 1 mM EDTA, 10 mM β-mercaptoethanol, 5% glycerol, pH 7.0) and assayed for GUS activity by fluorometric method as described by Jefferson, R. A., *Plant Mol. Biol. Rep.* 5:387–405 (1987).

Luciferase activity was measured by mixing 20 ul of cell-free extract with 200 ul reaction buffer containing 25 mM Tricine, 15 mM MgCl$_2$, 5.0 mM ATP, 0.5 mg/ml BSA and 7.0 mM β-mercaptoethanol, pH 7.8. One hundred ul of 0.5 MM luciferin (Sigma) was injected into the reaction mix and photon emission was recorded using a Moonlight 2010 luminometer (Analytical Luminescence).

Protein concentration in the cell-free extracts was measured with BCA protein assay kit (Pierce), using bovine serum albumin as standard.

B. Results

A 139 bp fragment of the MS-A upstream region is necessary and sufficient for expression.

Figure 1B:
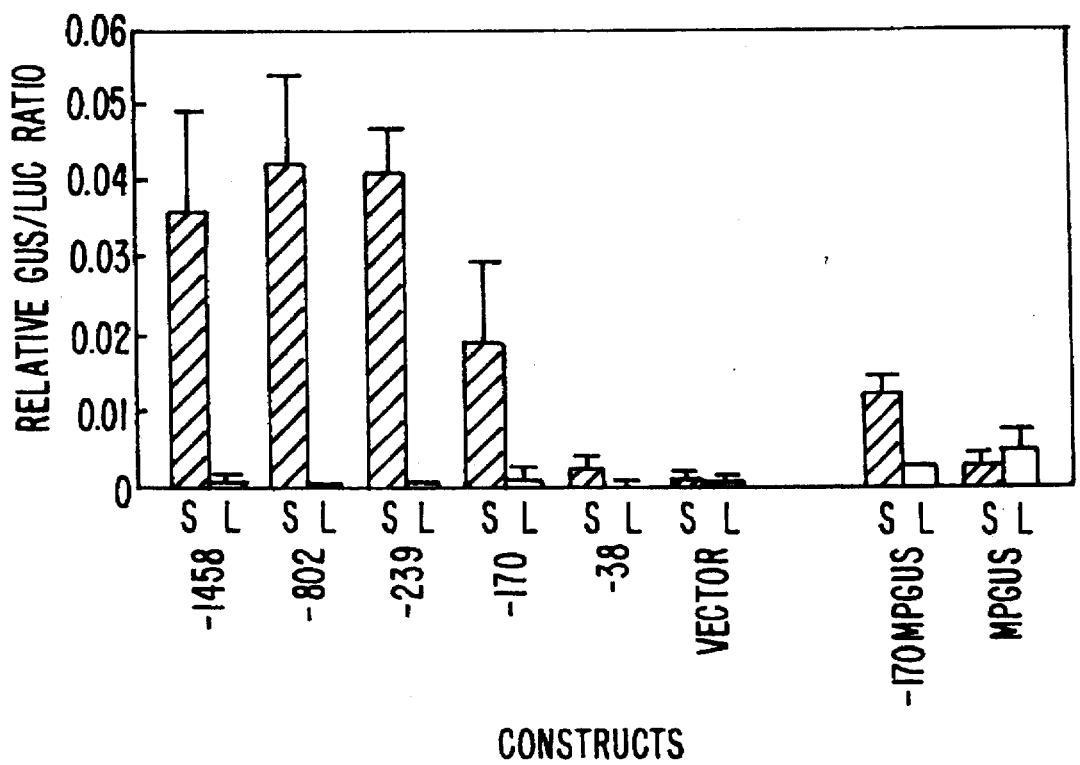
FIG. 1B shows transient expression of chimeric genes in seedlings and leaves. Three replicates were shot per construct per experiment. The relative GUS/LUC values reported are the average of 2–7 experiments using independently grown plant materials. Error bars refer to standard error of mean from 3 to 7 independent experiments.

Three replicate samples were bombarded per construct in each experiments. To compare the results from 2 to 7 independent experiments using the mean GUS/LUC ratio for each of the constructs was divided by the mean GUS/LUC ratio obtained for the expression of the positive control, CaMV35SGUS, in each experiment. The results obtained are shown in FIG. 1B.

The activity of the MSGUS chimeric gene with the longest 5' upstream region was monitored to test whether its expression in a transient expression assay is similar to that in whole plants. The result indicates that −1458MSGUS is highly expressed in seedlings but showed no activity in leaves above that of the vector alone. This result is in contrast with the expression of the positive control, CaMV35SGUS. CaMV35SGUS is highly expressed in both tissues (data not shown). The high level of expression of −1458MSGUS in seedlings and lack of activity in leaves bombarded with the same gene fusion agrees well with the differential activity of endogenous malate synthase promoters. This result indicates that the expression of the malate synthase gene in transient assays is similar to the expression of the gene in whole plants.

The effect of further deletions of the 5' flanking region on the activity of the MS-A promoter was also tested. Statistical analysis of the data using the two-tailed t-test did not show significant difference in the expression levels of −802MSGUS, −239MSGUS and −170MSGUS from that of −1458MSGUS at 99% confidence level. This result indicates that the removal of sequences upstream of −170 are not necessary for the activation of the gene in seedlings.

The deletion of sequences downstream of −170 to −38 relative to the transcription start site, however, eliminated GUS activity in seedlings. To ascertain that the deletion of the regulatory information between −170 to −38 was responsible for the lack of expression of −38MSGUS in seedlings and not due to a mutation in the reporter gene during subcloning, the B domain of the enhancer in the CaMV35S promoter was fused upstream of −38MSGUS (designated B−38MSGUS). The B domain contains the sequences between −343 to −90 of the CaMV35S promoter and has been shown to be able to confer high expression of a reporter gene in most cell types of the leaf, stem and root of transgenic plants. The results indicated that B−38MSGUS was very active not only in seedlings but also in leaves (data not shown). Since the deletion of 132 bp upstream of −38 eliminated expression, this result indicates that the region contains information necessary for the activation of the gene in seedlings.

To rule out the possibility that sequences downstream of the TATA box modulate the activity of malate synthase gene promoter, the region between −170 and −32 was tested to determine if MS-A contains sufficient information for the activation of the gene. A 139 bp fragment upstream of the putative TATA box sequence in MS-A gene was fused to a heterologous minimal promoter, MPGUS. MPGUS contains the TATA box of the CaMV35S promoter (−46 to +8) fused to GUS (Benfey, et al., *Embo. J.* 9:1677–1684 (1990)). MPGUS is not expressed in any tissue of transgenic plants. The upstream region from the malate synthase gene stimulated expression by 2.5-fold over and above that of MPGUS expression in seedlings, but not in leaves. This result suggests that the upstream region between positions −170 and −32 is not only necessary but also has sufficient information for the expression of the malate synthase gene in seedlings.

The −170 to −32 region of MS-A promoter contains sequences that are conserved in the 5' flanking DNA of the isocitrate lyase gene.

As shown in FIGS. 2A–D, several DNA motifs found in the −170 to −32 region of malate synthase MS-A promoter sequence are conserved in the 5' flanking region of the isocitrate lyase/ILA gene described below. The positions of these conserved sequences are shown relative to −170 to −1 of the MS-A promoter. Three GATA motifs located at −157, −145 and −132. Sixteen GATA motifs are also found at the 5' flanking DNA of isocitrate ILA gene. Mutational analysis of GATA motifs found in cab genes suggests that GATA elements may play a role in the modulation of the activity of the genes in response to light (Gilmartin, et al., *Plant Cell* 2:369–378 (1990)). DNA sequence between −162 to −152 (AAATAGATAAA) (SEQ ID NO: 5), which contains one of the GATA motifs, is similar to the 3AF1 binding site found in the pea rbcs −3A promoter. Several degenerate copies of the 3AF1 binding site are also found in ILA promoter (not shown). 3AF1 binding motifs have been implicated to be involved in the regulation of several light-regulated genes.

Fifteen out of the eighteen base pairs in position −123 to −106 of MS-A are identical in ILA (FIG. 2A). A copy of the 17 bp imperfect direct repeat found in positions −103 to −86 and −71 to −56 of MS-A is in positions −1474 and −1459 of HA (FIG. 2B). Furthermore, MS-A sequences ATCTCAG-GCA (at −77 to −68, SEQ ID NO: 6) and CAATGCAT (at −60 to −52, SEQ ID. NO: 7) are conserved in the region that is important for the activation of isocitrate lyase HA gene in transient assays (FIGS. 2C and D). Finally, a putative TATA box sequence is found at −30 of MS-A and at −24 of ILA relative to the transcription start site.

II. Activity of the *Brassica napus* malate synthase promoter in transgenic Arabidopsis.

A. Materials and Methods

1. Construction of Chimeric Genes

Figure 3:
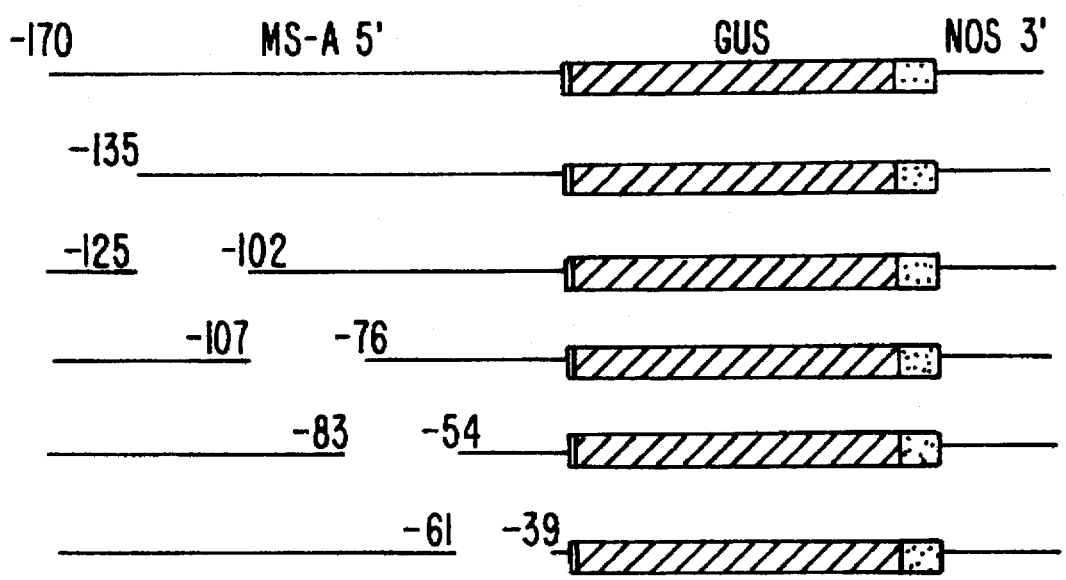
FIG. 3 is a diagrammatic representation of the chimeric constructs comprising internal deletions of the malate synthase promoter.

Internal deletions: The constructs −239MSGUS and −170MSGUS, which contain sequences from −239 to +31 or −170 to +31 of the upstream region of malate synthase MS-A gene fused to a bacterial β-glucuronidase gene, were generated as described above. Exonuclease HI deletion enzyme digestion of −239MSGUS was performed to generate a series of 5' deletions with terminal ends −134, −101, −75 and −38. Construct with 5' terminal ending at −53 was generated by deletion of sequences upstream of an Nsi I site at −54 relative to the transcription start site. The upstream region of MS-A 5' to the deleted sequences was amplified using −170MSGUS as template DNA. Because −170MSGUS was cloned in pBluescript II KS +/−vector (Stratagene), the M13 universal primer and another primer with sequences that are complementary to the MS-A promoter were used for PCR. To facilitate the cloning of the PCR product, a 15 nt adaptor sequence, 5'-CATGGATCCCAGCTC-3' (SEQ ID NO: 8) or 5'-TATGAGCTCGGATCC-3' (SEQ ID NO: 9), which contains the recognition sites for BamHI and SstI, was added to the 5' end of the primer with sequences complementary to the MS-A promoter sequence. For the nomenclature of the different constructs, D refers to internal deletion, and the numbers inside the parentheses are the position of the 5' and 3' ends of the promoter sequence that has been removed. The negative or positive sign before the numbers designate the position of the nt relative to the transcription start site. The upstream region of each construct was verified by DNA sequencing. The constructs are illustrated in FIG. 3.

D(−170/—135): This construct was generated by exonuclease III digestion of the 5' region of −239MSGUS.

D(−126/—102): The region from −170 to −127 of MS-A was amplified using the primer 5'-CATGGATCCGAGCTCATATCGGTTATGATTATCTC-3' (SEQ ID NO: 10), which has sequences complementary to MS-A sequence at −127 to −146. The amplified fragment was fused upstream of −102MSGUS. The 36 bp deleted sequence between −126 and −102 was replaced by a 4 bp DNA with the following sequence, 5'-GCTC-3' (SEQ, ID, NO. 11).

D(−107/−76): The upstream region from −170 to −108 of MS-A was amplified using primer 5'CATGGATCCGAGCTCTATGTATGCTTTTCGTCATC-3' (SEQ ID NO: 12), which has sequences complementary to MS-A sequence at −108 to −127. The amplified fragment was ligated upstream of −75MSGUS. The 32 bp sequence between −107 and −76 was deleted and replaced by a 7 bp DNA with the following sequence, 5'-GACTCCA-3' (SEQ ID NO: 13).

D(−83/—54): The upstream region from −170 to −84 of MS-A was amplified using primer 5'CTAGGATCCGAGCTCATCATTGGGGATGTGTGCC-3' (SEQ ID NO: 14), which has sequences complementary to MS-A sequence at −84 to −103. The amplified fragment was ligated upstream of −53MSGUS. The 30 bp sequence between −83 and −54 was deleted and replaced by a 43 bp DNA with the following sequence, 5'GAGCTCCACCGCG GTGGCGCCGTCTAGAACTAGTGGATCCCCC-3' (SEQ ID NO: 15).

D(−61/−39): The upstream region from −170 to −62 of MS-A was amplified using the primer 5'TATGAGCTCGGATCCATGTGTGCCTGAGATTCAG-3' (SEQ ID NO: 16), which has sequences complementary to MS-A sequence at −62 to −81. The amplified fragment was ligated upstream of −38MSGUS. The 23 bp sequence between −61 to −39 was deleted and replaced with a 9 bp DNA with the following sequence, 5'-GATCCGAGC-3' (SEQ ID NO: 17).

2. Plant Transformation

Malate synthase chimeric genes were inserted into a binary vector, GA482, and mobilized into *Agrobacterium tumefaciens* EHA101 by triparental mating. *Arabidopsis thaliana* (ecotype C24) plants were transformed using the root explant procedure described by Valvekens, et al., *Proc. Natl. Acad. Sci. USA* 85:5536–5540 (1985). T1 seeds from the initial transformant (T0) were germinated on kanamycin plates and transferred to soil and grown at 22° C. under continuous light. T2 seeds were collected and used for further analysis.

3. Biochemical Assays

Malate synthase activity in Arabidopsis seeds and seedlings was measured in cell-free extracts as described by Koller, et al., *Arch. Bioch. Bioph.* 181:236–248 (1977) except that 100 mm MOPS (pH 8.2) was used for preparing the reaction buffer.

Fluorogenic assays of GUS enzyme activity in cell-free extracts and histochemical staining in vivo was as described by Jefferson, R. A., *Embo. J.* 6:3901–3907 (1987) except that methanol was added to a final concentration of 20% to reduce the background caused by endogenous activities in the plant material.

Protein concentration in the cell-free extracts was measured using the BCA protein assay kit (Pierce). To reduce the interference in the protein assay caused by β-mercaptoethanol in the GUS extraction buffer, samples were preincubated with equal volume of 0.1M iodoacetamide in 0.1M Tris buffer, pH 8, for 20 min at 37 C. (Hill, et al., *Analytical Biochem.* 170:203-208 (1988)). Bovine serum albumin was used as the standard.

B. Result

Deletion of 5' flanking regions defines embryo-specific positive and negative regulatory elements.

GUS activity was detected both in dry seeds and seedlings but not in young leaves of the 9 independently Transformed plants with the –1458MSGUS construct that were analyzed. Because dry seeds are quiescent, the activity of the malate synthase gene promoter in dry seeds is assumed to be a reflection of its activity during late embryogenesis. In every line examined, the activity in seedling was always higher than the activity in dry seeds. This pattern of promoter activation parallels the expression of the endogenous malate synthase genes in *Brassica napus* during development.

The regulated expression of –1458MSGUS in transgenic Arabidopsis indicates that the control elements in the malate synthase gene promoter are located in the sequences downstream of –1458. To begin to localize these elements, the effects of 5' terminal deletions on the activity of the promoter was examined. GUS activities in dry seeds, 2 DAI etiolated seedlings and young leaves were measured to test whether the deletion mutations affect the expression of the gene during development. Due to the high variation in expression between independently Transformed plants containing the same construct, the non-parametric Mann-Whitney statistical test was used to assess whether differences in expression between constructs were significant (Table 1).

TABLE 1

|         |      | –1458 MS | –802 MS | –239 MS |
|---------|------|----------|---------|---------|
| –802 MS | SEED | D        |         |         |
|         | SDLG | S        |         |         |
| –239 MS | SEED | S        | D       |         |
|         | SDLG | S        | S       |         |
| –170 MS | SEED | S        | S       | S       |
|         | SDLG | S        | S       | S       |

The results indicate that the deletion of the region between –1458 to –803 significantly reduced the activity of the gene in dry seeds but not in seedlings. This suggests that at least one positive regulatory element that specifically modulates the expression of the malate synthase gene in embryos is present in this region. In contrast, further deletion of the region from –802 to –240 reversed the effect of the previous deletion. The level of expression of –239MSGUS in embryos is similar to that of –1458MSGUS. This result implies that a negative element lies within –802 to –240. Comparable expression of the three constructs in seedlings implies that these positive and negative regulatory elements located upstream of –239 specifically modulate the expression of the gene only during late-embryogenesis.

Further deletion of the upstream region up to –170 did not affect the expression of the gene relative to –1458MSGUS. In addition, the time course of –170MSGUS expression during germination and postgerminative growth in the dark and in the light was similar to that of –1458MSGUS (data not shown). These results indicate that the control elements required for the developmental expression of the malate synthase gene are located downstream of –170.

Deletion of sequences up to –38 eliminated GUS activities in seeds, seedlings and in young leaves. Moreover, not a single seedling stained in all the lines containing –38MSGUS examined even after three days of incubation with GUS histochemical solution (dam not shown). It was therefore concluded that DNA sequences from –170 to –38 contain information necessary for the activation of the malate synthase MS-A gene both during late embryogenesis and postgerminative growth.

Figure 4A:
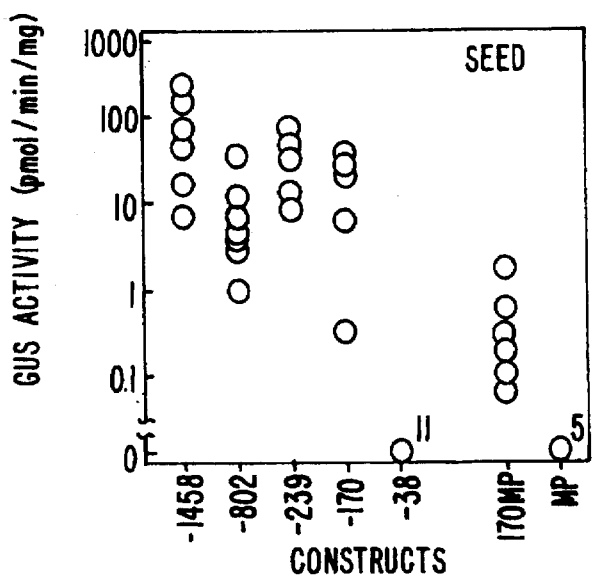
FIGS. 4A–4C show expression of malate synthase chimeric genes in transgenic Arabidopsis seeds (FIG. 4A) seedlings (FIG. 4B) and leaves (FIG. 4C). The number printed close to the symbol at the zero level indicates the number of independently transformed lines that did not exhibit significant GUS activity. The number of independently transformed plants analyzed per construct were as follows: −1458MSGUS, 9; −802MSGUS, 9; −239MSGUS, 8; 170MSGUS, 10; −38MSGUS, 11; −170MPGUS, 11; MPGUS, 5.
Figure 4B:
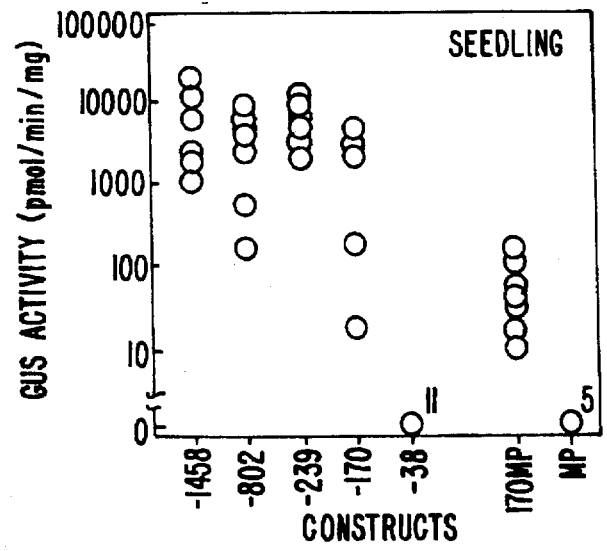
Figure 4C:
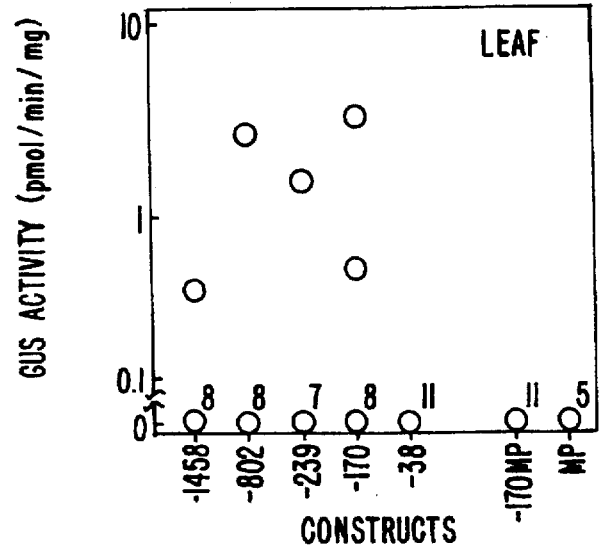

A 139 bp fragment from positions –170 to –32 of the malate synthase gene, MS-A, was fused to the CaMV35S (–46 to +8) minimal promoter attached to GUS construct (designated –170MPGUS). FIG. 4 shows that expression was detected in dry seeds, was increased was in seedlings and was absent in young leaves. In contrast, the CaMV35S minimal promoter alone, MPGUS, was not expressed in the three stages of plant development tested.

To further examine whether the 139 bp fragment of the upstream region of the malate synthase can direct the proper temporal and spatial expression of the reporter gene, the kinetics and the histochemical localization of GUS activity in transgenic Arabidopsis lines containing –170MPGUS were analyzed. As shown in FIG. 4, the –170MPGUS pattern of temporal expression in seedlings grown in the dark and in the light is virtually the same as –170MSGUS. The localization of GUS activity in 2 DAI etiolated seedlings of –170MPGUS was similar to –170MSGUS. In contrast, MPGUS did not stain even after three days of incubation with GUS histochemical solution.

These results demonstrate that the sequences between –170 to –32 of the promoter have not only necessary but also sufficient information for the activation of the malate synthase gene both during late embryogenesis and postgerminative growth.

Analysis of internal deletions identifies a domain required for the activation of MS-A gene in seedlings.

Figure 5A:
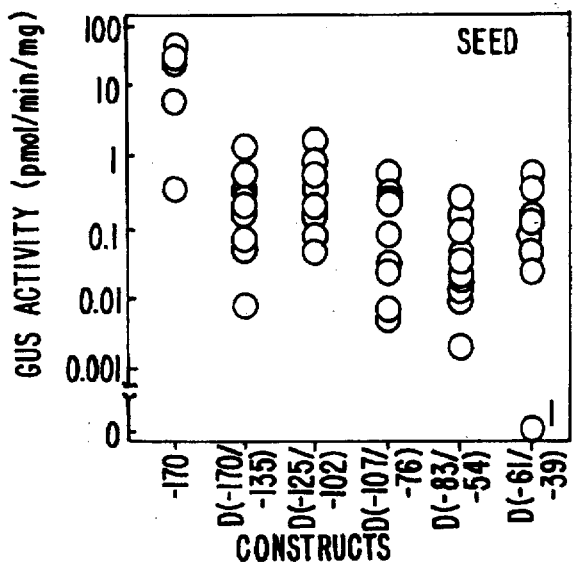
FIGS. 5A–5C show internal deletion analysis of the minimal B. napus malate synthase promoter in seeds (FIG. 5A), seedlings (FIG. 5B) and leaf (FIG. 5C). The number of lines of independently transformed plants analyzed per construct were as follows: −170MSGUS, 10; D(−170/−135), 15; D(−125/−102), 14; D(−107/−76), 10; D(−83/−54), 13; D(−62/−39), 14.
Figure 5B:
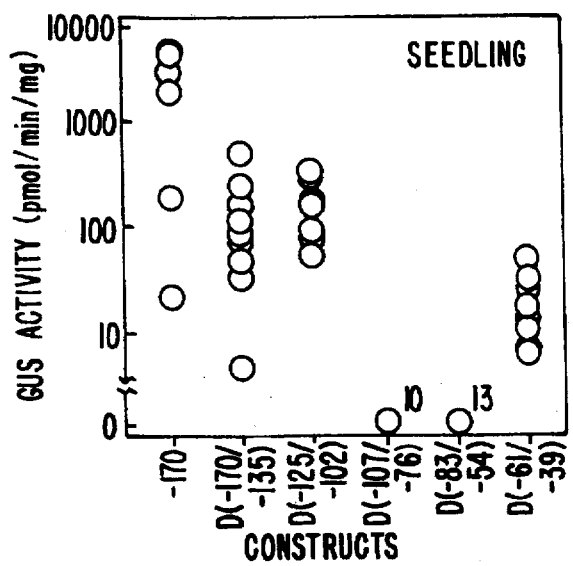
Figure 5C:
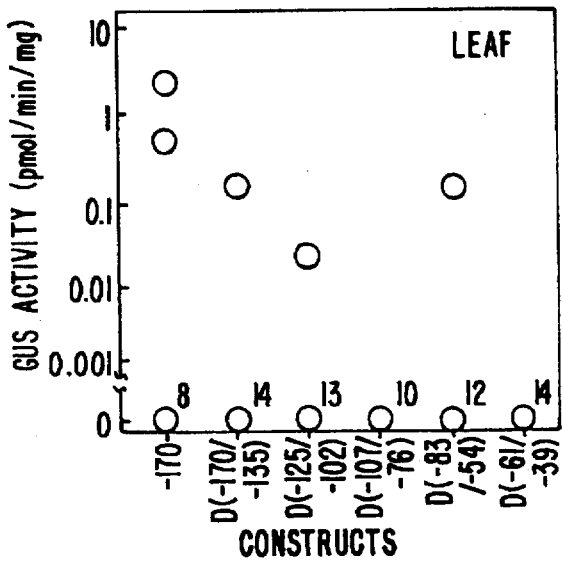

To determine the functional significance of the GATA motifs and other 5' sequences noted in Section I, above, the effects of a series of small (about 30 bp) terminal and internal deletions on the activity of the promoter of MS-A gene were investigated. The effect of the deletions on the expression of the malate synthase gene during development was assayed by measuring GUS activities in seeds, seedling and leaves of transgenic Arabidopsis. The result from 75 independently transformed plants analyzed is shown in FIGS. 5A–C. The statistical analysis of the data using the Mann-Whitney test is shown in Table 2.

TABLE 2

|              |      | –170 MS | D(–170/–135) | D(–125/–102) | D(–107/–76) | D(–83/–54) |
|--------------|------|---------|--------------|--------------|-------------|------------|
| D(–170/–135) | SEED | D       |              |              |             |            |
|              | SDLG | D       |              |              |             |            |
| D(–125/–102) | SEED | D       | S            |              |             |            |
|              | SDLG | D       | S            |              |             |            |
| D(–107/–76)  | SEED | D       | S            | D            |             |            |
|              | SDLG | D       | D            | D            |             |            |
| D(–83/–54)   | SEED | D       | D            | D            | S           |            |
|              | SDLG | D       | D            | D            | S           |            |

TABLE 2-continued

|  |  | −170 MS | D(−170/−135) | D(−125/−102) | D(−107/−76) | D(−83/−54) |
|---|---|---|---|---|---|---|
| D(−61/−39) | SEED | D | S | D | S | S |
|  | SDLG | D | D | D | D | D |

The results indicate that the 5' terminal deletion of sequences upstream of −135 did not eliminate the expression of the gene during late embryogenesis and postgerminative growth. Although significantly reduced, the pattern of expression of the D(−170/−135) construct was similar to that of −170MSGUS. This result suggests that the 3AF1 and two GATA motifs found upstream of −134 are not required for the activation of the gene in the seed and seedling.

Similarly, the expression of the chimeric gene D(−125/−102), although lower than that of −170MSGUS, can be detected in dry seeds, becomes induced during germination, and is not expressed in leaves. This result indicates that the region between −125 to −102, which has the sequence ACGAAAAGCATACATAAC (SEQ ID NO: 18) also found in isocitrate lyase ILA gene, is not necessary for the activation of the promoter in seed or in seedling.

Deletion of the sequences from −61 to −39 reduced the activity of the promoter dramatically but the D(−61/−39) chimeric gene still showed a pattern of expression similar to that of −170MSGUS. The deleted region contains the sequences ATCTCAGGCA (SEQ ID NO: 6) and CAATGCATA (SEQ ID NO: 19), which are conserved in the region found to be operational in the activation of *Brassica napus* isocitrate lyase ILA gene in transient assays. This result indicates that these DNA motifs are not required for the activation of the malate synthase gene.

The constructs D(−107/−76) and D(−83/−54), each containing only one copy of the 17 bp imperfect direct repeat, eliminated GUS activity in seedlings but not in seeds. Furthermore, 2 DAI etiolated seedlings of all transgenic lines containing these two constructs did not stain even after three days of incubation with the substrate for histochemical localization of GUS activity (data not shown). In contrast, 2 DAI seedlings of D(−170/−135), and D(−125/−102) and D(−61/−39) stained blue just after a few hours of incubation with the GUS activity histochemical. It is clear that the deleted region between −107 to −76 and −83 to −54 is critical for the activation of the gene in seedlings, but not during embryogenesis.

Figure 6A:
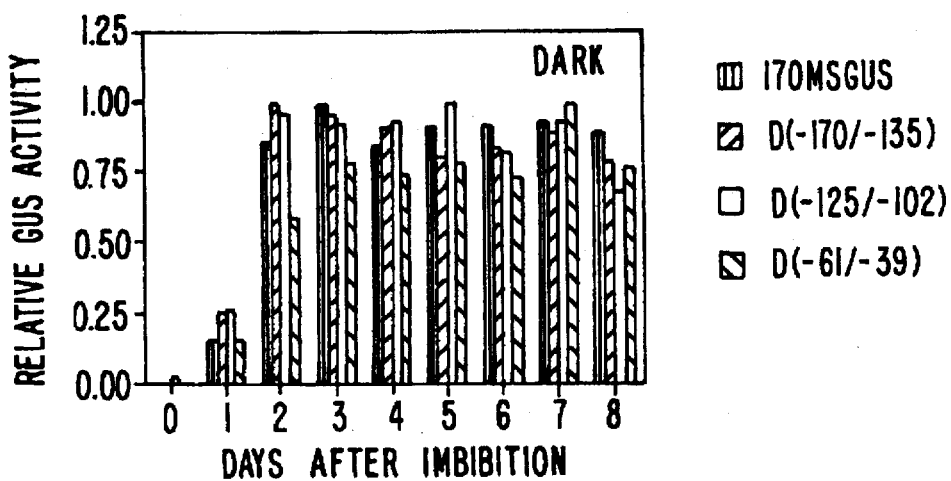
FIGS. 6A–6C show the effect of internal deletions on the temporal expression of malate synthase MS-A promoter. Malate synthase and GUS activities were measured in cell-free extracts from dry seeds (0 DAI) and seedlings germinated either in the dark (FIG. 6A) or in the light (FIG. 6B).
Figure 6B:
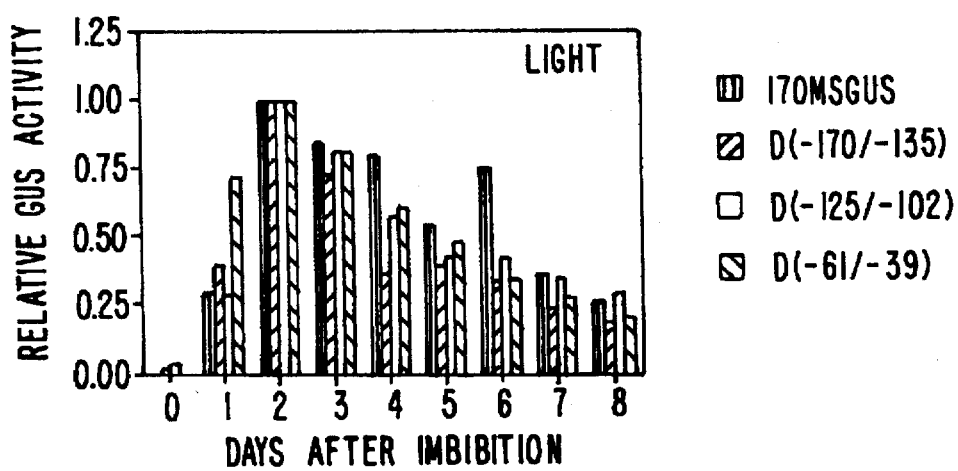
Figure 6C:
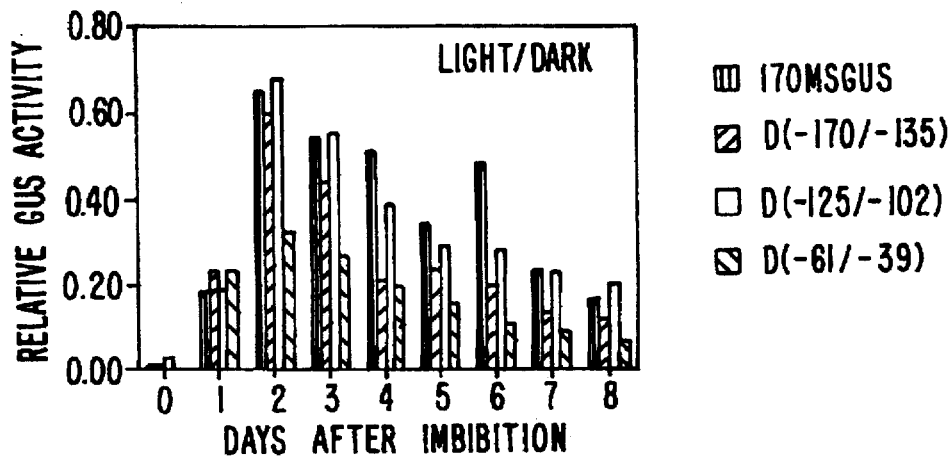

To determine whether the internal deletions affect the timing of malate synthase gene activation and induction during germination and postgerminative growth the time course of GUS activities in seedlings grown in the dark and in the light. As shown in FIGS. 6A–C, the expression of the constructs D(−170/−135), D(−125/−102) and D(−61/−39) in transgenic Arabidopsis showed a similar pattern of expression as −170MSGUS both in the dark (FIG. 6A) and in the light (FIG. 6B). In seedlings grown both in the dark and in the light, GUS activity was induced during germination and peaked at 2 to 3 DAI. Similarly, after 3 DAI, GUS activity in seedlings grown in the dark remained high, whereas GUS activity in seedlings grown in the light gradually declined. Moreover, the levels of GUS activities in the seedlings grown in the dark were always higher than the GUS activities in seedlings grown in the light (FIG. 6C). In contrast, the expression of D(−107/−76) and D(−83/−54) was detected only in dry seeds but not during germination and postgerminative growth for both seedlings grown in the dark and in the light (dam not shown). This indicates that the deletion of the sequences at −107 to −76 or −83 to −54 totally removed or disrupted the control elements required for the activation of the gene in seedlings.

EXAMPLE 2

Analysis of isocitrate lyase promoter sequences

Particle gun-mediated gene transfer and stable plant transformation were used to delineate sequence elements that activate the isocitrate lyase gene promoter in various tissues. Zhang, et al. (*Plant Physiol.* 104:857–864 (1994)) have previously shown that the 5' flanking region of the isocitrate lyase gene is sufficient and that the 3' flanking region is not necessary for the correct spatial and temporal regulation of the isocitrate lyase gene in transgenic tobacco plants. A series of deletions in the promoter of ILA was generated to localize the DNA sequences required for expression.

A. Materials and Methods

1. Plant Material and Culture Media.

*Brassica napus* L. (rapid cycling base population, CrGC5) embryos and seedlings were grown as previously described (Harada, et al., *Mol. Gen. Genet.* 212:466473 (1988)). Arabidopsis plants were grown in a growth room with continuous light at 22° C. For particle gun experiments, late stage embryos (ca. 45 days post anthesis) from *Brassica napus* were dissected from their seed coat, and placed on modified Monnier embryo culture medium (Monnier, et al., *Rev. Cytol. Biol. Veg.* 39:1–120 (1976)) with 12.5% sorbitol, 10 µM ABA, and 0.8% agar. The embryos were used for bombardment in the same day. For particle gun experiments with seedling cotyledons, *B. napus* seeds were sterilized prior to germination. The seeds were first rinsed in 95% ethanol for 2 min., blotted dry with Kimwipes, stirred in 20% Clorox bleach containing a drop of Tween 20 for 45 rain, and rinsed 3 times with sterile distilled water. The seeds were sowed on plates containing ½ MSO media (see below) with 0.8% agar; and kept at 25° C. in the dark for 3 days. The cotyledons were then excised and placed on ½ MSO media, and used for bombardment on the same day. For leaves, the second or third leaves of greenhouse grown *B. napus* were surface sterilized with 2% bleach with a drop of Tween 20 for 10 min, rinsed 3 times with sterile distilled water, and placed upside down on ½ MSO plates. The leaves were either used the same day for bombardment, or left at 25° C., 16 hour light period overnight before bombardment. ½ MSO media: 2.2 g/l MS salts and 50 µg/ml myo-inositol, 5 µg/ml thiamine HCl, 0.5 µg/ml nicotinic acid, and 0.5µg/ml pyridoxine HCl. (Gamborg, et al., *Exp. Cell Res.* 50:151–158 (1968)). Monnier embryo culture medium with modifications is: 1.9 g/l $KNO_3$, 825 mg/l $NH_4NO_3$, 170 mg/l $KKH_2PO_4$, 880 mg/l $CaCl_2 \cdot 2H_2O$, 370 mg/l $MgSO_4 \cdot 7H_2O$, 350 mg/l KCl, 12.4 mg/l $H_3BO_4$, 33.6 mg/l $MnSO_4 \cdot H_2O$, 21.0 mg/l $ZnSO_4 \cdot 7H_2O$, 1.66 mg/l KI, 0.5 mg/l $Na_2MoO_4 \cdot 2H_2O$, 0.05 mg/l $CuSO_4 \cdot 5H_2O$, 0.05 mg/l $CoCl_2 \cdot 6H_2O$, $10^{-4}$ mg/l thiamine HCl, $10_{-4}$ mg/l pyridoxine HCl, 400 mg/l glutamine, 14.9 mg/l $Na_2EDTA$, 11.1 mg/l $FeSO_4 \cdot 7H_2O$, 10.27 g/l sucrose, pH 5.5.

2. Plasmid Construction.

Constructs were all based on −3500IL/GUS/IL (previously designated IL/GUS/IL, Zhang, et al., *Plant*

*Physiol* 104:857–864 (1994)). The constructs −2700IL/GUS/IL, −1700IL/GUS/IL, −590IL/GUS/IL, −390IL/GUS/IL, were obtained through Exonuclease III deletion experiments, whereas −2700(1200-590), −2700 (590-350), −2700(350-30), −1200(1200-30), −1200IL/GUS/IL, −350IL/GUS/IL, −30IL/GUS/IL, were made using restriction enzyme recognition sites. The constructs are illustrated in FIG. 7.

3. Particle Gun and Enzyme Assays.

Transient assays were done with a particle gun (Flowtech Engineering). The speed of the macroprojectiles was controlled by pushing the macroprojectiles to different depth in the gun barrel. The depth (in 0.5 cm increments) that resulted in the highest GUS activity in tobacco suspension culture cell was used for all the experiments (Klein, et al., *Bio/Technology* 6:559–563 (1988)). The procedures for precipitating plasmid DNA on the projectiles were as described above. GUS and luciferase activity were assayed as described above.

4. Arabidopsis Transformation.

*Arabidopsis thaliana* (ecotype BeO) plants were transformed using the root explant procedure using transformation vector GA482 as described above. $T_1$ seeds from $T_0$ plants (the original transformants) were collected, and germinated on media containing kanamycin. The kanamycin-resistant seedlings were transplanted to soil, from which the T2 seeds were collected. Only plants that did not have obvious rearrangements of the transgenes on Southern blots were chosen for the study. GUS assays were done on T2 seeds and seedlings. Leaves were from T2 plants grown for 18 days in continuous light.

B. RESULTS

Putative positive element in the 5' flanking region uncovered in transient assay.

Figure 8A:
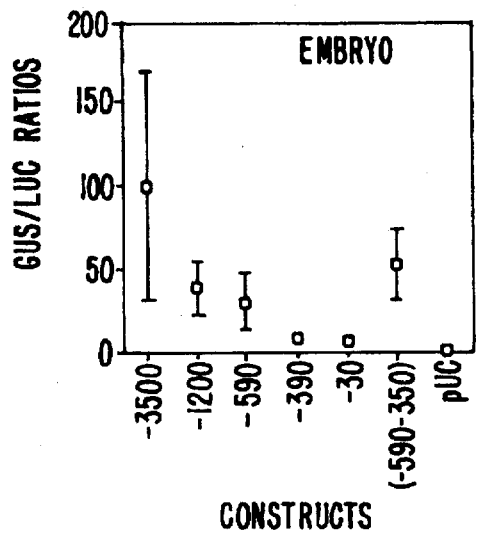
FIGS. 8A–8C show relative GUS/Luc ratios of chimeric constructs in transient assays in embryo (FIG. 8A), seedling (FIG. 8B), and leaf (FIG. 8C).
Figure 8B:
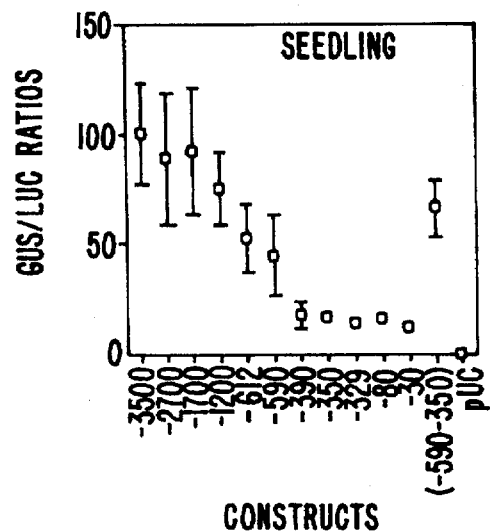
Figure 8C:
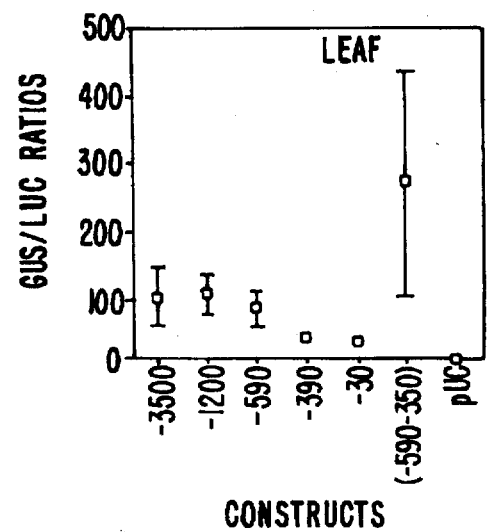

FIGS. 8A–C shows the results of transient assays using the constructs described above. These data show that deletions downstream of −3500 till −390 resulted in a gradual decrease in GUS/Luc ratio in seedling cotyledons, suggesting that quantitative or redundant positive elements acting in seedlings were located in the deleted region. The closest positive element(s) to the gene were within −590 to −390, the deletion of which reduced the promoter activity to ½ to ⅓, and further deletions downstream of −390 did not affect the promoter activity appreciably (FIG. 8B).

To investigate if the same element(s) were also active in the embryos, the constructs were also bombarded into late stage (ca. 45 days post anthesis) embryos. FIG. 8A shows that the profiles of normalized activities in embryos were similar but not identical to those in seedlings (compare FIGS. 8A and 8B). Similar to the results obtained in seedlings, the deletion of the region between −590 and −390 decreased the promoter activity to ¼ in embryos (FIG. 8A). Further deletion downstream of −390 did not have significant effect.

FIG. 8C shows the results from leaves. Although most of the constructs were less active in the leaves than in seedlings, deletion between −590 to −390 also resulted in a drop of GUS/Luc ratio in the leaves (FIG. 8C). To determine the developmental specificity of the region between −590 to −350, the fragment was fused with construct −30IL/GUS/IL to create construct −(590-350)MPIL/GUS/IL. Because construct −30IL/GUS/IL contained only 3 bp in addition to the putative TATA box, it was considered to be an isocitrate lyase minimal promoter. When bombarded into the plants by the particle gun, the −590 to −350 fragment activated the IL minimal promoter in embryos, seedling cotyledons, as well as leaves (FIGS. 8A–8C). The results from transient assays suggested that fragment −(590–350) contains a constitutive positive element, since it was capable of activating gene expression in embryos, seedlings, and leaves.

Particle gun transient assay results are not confirmed by transgenic experiments.

Figure 9A:
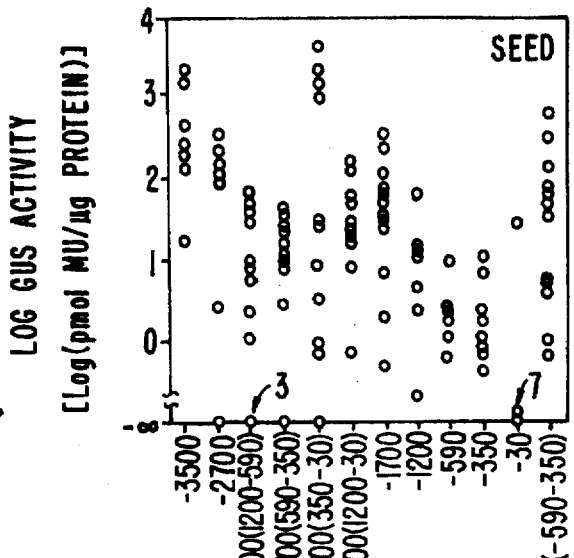
FIGS. 9A–9C show the log of GUS activity in transformed Arabidopsis plants.
Figure 9B:
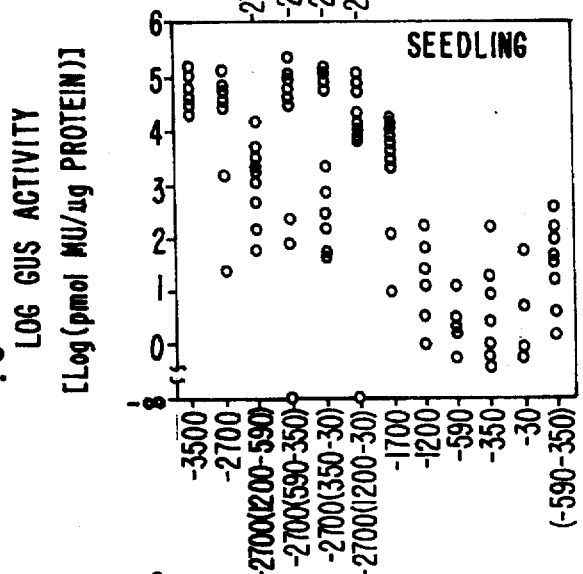

To determine whether the expression of genes in the transient assay reflects the expression of the same genes in vivo, the constructs −3500IL/GUS/IL, −1200IL/GUS/IL, −590IL/GUS/IL, −350IL/GUS/IL, −30IL/GUS/IL, and −(590–350)MPIL/GUS/IL were transformed into Arabidopsis plants. GUS activities from the seedlings, seeds, and leaves of the $T_2$ transgenic plants were measured. FIGS. 9A and 9B show the GUS activities in 2 DAI seedlings and dry seeds, respectively, of independently-transformed Arabidopsis plants. As described in Example 1, above, the Mann-Whitney test was used to examine if there are significant differences between the expression of different deletion constructs. The results of the comparisons (5% significance level) are shown in Table 3.

TABLE 3

Pair-Wise Comparison of GUS Activities of Transgenic Arabidopsis Plants Using Mann-Whittney Test (5% Significance Level)

| | SEED | SEEDLING |
|---|---|---|
| 3500/2700 | different | same |
| 2700/1700 | different | different |
| 1700/1200 | different | different |
| 2700/2700(1200-590) | different | different |
| 2700/2700(590-350) | different | same |
| 2700/2700(350-30) | same | same |
| 2700/2700(1200-30) | different | same |

Figure 9C:
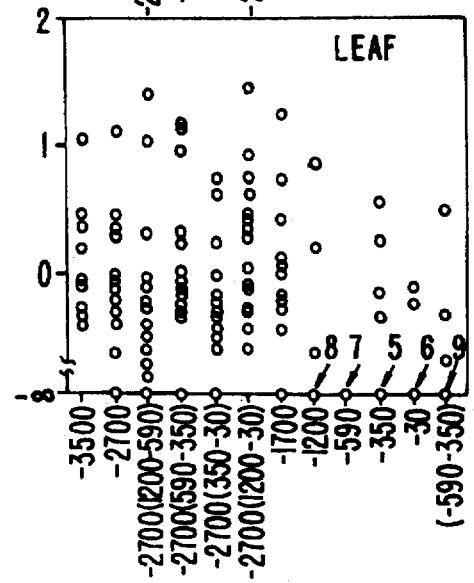

Deletion of the region between −3500 and−1200 had the most dramatic affect on the activity of the isocitrate lyase promoter in transgenic plants. The activity of −3500IL/GUS/IL was higher than that of −1200IL/GUS/IL by ca. 50 fold in embryos and ca. 1800 fold in seedlings. Therefore, quantitative element(s) that significantly affect the transcription activity of the isocitrate lyase gene resided between −3500 and −1200. In addition, there were no significant differences in GUS activities of seedlings and seeds among plants transformed with constructs −590IL/GUS/IL, −350IL/GUS/IL and −30IL/GUS/IL (Table 3). These results from transgenic plants are in direct contrast to the activities of the same constructs in transient assays. Activity of −3500IL/GUS/IL, differed from that of −1200IL/GUS/IL by only 25% and 60% in seedlings and embryos, respectively. Statistical tests showed that −590IL/GUS/IL is significantly greater than −350IL/GUS/IL in transient assay, whereas no significant differences between the two constructs existed in transgenic plants (Table 3). Furthermore, construct −(590–350)-MPIL/GUS/IL was expressed at high levels in embryos, seedlings, and leaves in the particle gun transient assay. In contrast, no significant GUS activity was found in leaves transformed leaves transformed with construct −(590–350)MPIL/GUS/IL. FIG. 9C), had high activities in seeds and seedlings of transgenic plants (FIGS. 9A, B). Therefore, under the conditions used here, the same constructs had different activities in transient assays and transgenic plants.

Distinct embryo specific elements are present at the 5' flanking region of the isocitrate lyase gene.

Because enhancer element(s) that have the most dramatic effects on the expression of the gene is located beyond −1200 bps, the loss of the element(s) have greatly reduced the sensitivity of the deletion analysis down stream of −1200. To overcome this problem, constructs were made in which the upstream sequence up to −2700 was kept and internal deletion of the region under question were made (FIG. 7). These constructs were transformed into Arabidopsis plants, and GUS activities were measured in seedlings, seeds, and leaves.

The data are shown in FIGS. 9A–C. FIGS. 9A and 9B show that the deletions of 2700–1700, 1700–1200, and 1200–590 affected the expression of the gene in both seeds and seedlings, indicating that these regions may contain both seed and seedling activating sequences. In contrast, deletion 3500 −2700 and the internal deletion of 590–350 from 2700IL/GUS/IL, which resulted in construct 2700(590350) IL/GUS/IL, affected the expression of the gene in only seeds while had not effect on the expression in seedlings. This result suggested that sequences between −3500 to −2700 and −590 to −350 contained an element(s) that is specific for embryo. The internal deletion of 350–30 from 2700IL/GUS/IL, which resulted in construct 2700(350-30)IL/GUS/IL, did not affect the expression of the gene in either seed or seedling, indicating that the region between 350 to 30 is not import for the expression of the isocitrate lyase gene in seed or seedling.

In order to compare the levels of gene expression in seedlings and seeds, the ratios of GUS activities from seedlings and seeds of each transformants were determined. These ratios, as well as the median ratio of each construct are shown in Table 4. The seedling to seed ratios indicate the relative strength of the seedling specific elements vs. seed specific elements in the upstream region of the construct. Consistent with the observation that 590 to 350 contains an embryo specific element, only −(590–350)MPIL/GUS/IL showed higher levels of GUS activity in seed compared with that of seedling (Table 4). The same point is also illustrated by the extremely high seedling to seed ratios of construct 2700 (590–350)IL/GUS/IL (Table 4). Table 4 also shows that seedling dominant elements exist between 1700 and 1200. The expression of construct 1700IL/GUS/IL in seedlings are on avenge 200 times higher than that in seed, whereas there is only a 2 fold difference in seedling/seed activities with construct 1200IL/GUS/IL. All together, these results implied that the activation of the isocitrate lyase gene in embryo and seedling are mediated at least in part by embryo and seedling specific cis-acting sequences. Again, very low levels of GUS activity was found in the leaves of the transgenic plants.

TABLE 4

Medians and Means of Seedling GUS Activity/Seed GUS Activity Ratios of Transgenic Arabidopsis Plants

|  | Medians | Means | n |
| --- | --- | --- | --- |
| 3500 | 120 | 260 | 14 |
| 2700 | 380 | 390 | 13 |
| 2700(1200-590) | 220 | 250 | 9 |
| 2700(590-350) | 3900 | 3300 | 13 |
| 2700(350-30) | 47 | 74 | 12 |
| 2700(1200-30) | 730 | 640 | 15 |
| 1700 | 210 | 190 | 16 |
| 1200 | 2.8 | 3.3 | 10 |
| 590 | 1.2 | 1.2 | 7 |
| 350 | 1.6 | 4.6 | 9 |
| 30 | 7.7 | 23 | 8 |
| 590-350 | 0.74 | 0.86 | 12 | n: Number of plants analysed

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An expression cassette comprising an isocitrate lyase promoter operably linked to a heterologous nucleic acid sequence, wherein the promoter selectively hybridizes to a Brassica isocitrate lyase promoter.

2. The expression cassette of claim 1, wherein the promoter is from Brassica.

3. The expression cassette of claim 1, wherein the promoter is SEQ ID NO:2.

4. The expression cassette of claim 1, wherein the promoter comprises a sequence extending from about −2700 to about −1700 of a isocitrate lyase promoter.

5. The expression cassette of claim 4, wherein the promoter comprises a sequence extending from about nucleotide 102 to about nucleotide 1102 of SEQ ID NO:2.

6. The expression cassette of claim 1, wherein the promoter comprises a sequence extending from about −1700 to about −1200 of a isocitrate lyase promoter.

7. The expression cassette of claim 6, wherein the promoter comprises a sequence extending from about nucleotide 1102 to about nucleotide 1602 of SEQ ID NO:2.

8. The expression cassette of claim 1, wherein the promoter comprises a sequence extending from about −1200 to about −590 of a isocitrate lyase promoter.

9. The expression cassette of claim 8, wherein the promoter comprises a sequence extending from about nucleotide 1602 to about nucleotide 2212 of SEQ ID NO:2.

10. The expression cassette of claim 1, wherein the promoter comprises a sequence extending from about −590 to about −350 of a isocitrate lyase promoter.

11. The expression cassette of claim 10, wherein the promoter comprises a sequence extending from about nucleotide 2212 to about nucleotide 2452 of SEQ ID NO:2.

12. A transgenic plant comprising the isocitrate lyase promoter of claim 1 operably linked to a heterologous nucleic acid sequence.

13. The transgenic plant of claim 12, wherein the promoter is SEQ ID NO:2.

14. The transgenic plant of claim 12, wherein the plant is a member of the Brassica family.

15. A method of expressing a heterologous nucleic acid sequence in a plant comprising:

a) introducing into plant tissue a vector comprising the isocitrate lyase promoter of claim 1 operably linked to the heterologous nucleic acid sequence; and b) regenerating the plant tissue into a whole plant.

16. The method of claim 15, wherein the plant tissue is from a member of the Brassica family.

17. The expression cassette of claim 1, wherein the promoter is no more than 3000 nucleotides in length.

18. The transgenic plant of claim 12, wherein the promoter is no more than 3000 nucleotides in length.

19. The method of claim 15, wherein the promoter is no more than 3000 nucleotides in length.

* * * * *

UNITED STATES PATENT AND TRADEMARK OFFICE
CERTIFICATE OF CORRECTION

PATENT NO.     : 5,689,040
DATED          : November 18, 1997
INVENTOR(S)    : John J. Harda and James Z. Zhang It is certified that error appears in the above-identified patent and that said Letters Patent is hereby corrected as shown below:

<u>Title page,</u>
Item [75], please delete inventor "Debbie Laudencia-Chingcuanco"

Signed and Sealed this

Fifth Day of August, 2003

JAMES E. ROGAN
*Director of the United States Patent and Trademark Office*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 1789 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
GAGAGAGGAT  CCAGAGATTA  TCAACACGTG  GGAGCTTATG  GAAGATCTCG  AAGATTCAAC       60

GAAGATTAGT  CCCAAATCTC  GTGGGATCTT  CGGGAAATCA  TGGAAGACTC  CGGTGAAATC      120

GATTGTTGAA  TCTCCTAAGA  GGAATGGTAG  TAGTAAGAGA  TTCAGGGGAA  AAGAAAACAG      180

AGGAGAGAAA  CAGAGTCCGA  ACCAGATTCT  GAAGACTCCA  AAGAGAGGCG  TGATGCGTTT      240

GAGTTTCCTC  TACAAATCAG  AAGAGATTAC  GCAGAGGAGG  AGGAAGAGTT  TCAGTCCAAT      300

GTTCGATCCA  GACCTCGTGG  CTTCTTACGA  GAGGGAGTTG  TCTCAGGAGA  AAGAACAGAT      360

CAAGATGGTG  ATCTCTCCTC  CAGACCCTCT  CCCGGAGAAT  GTCCGCCGGG  AGGAGAGAAC      420

TCGGTGGTCG  TCTACATAAC  GACGCTGAGA  GGGATCAGGA  AGAGCGTTCG  AGGACTGCAA      480
```

-continued

| | | | | | |
|---|---|---|---|---|---|
| CGCGGTGAGA | TCGATACTGA | TTCGCACGAG | GTTCGGTACT | CGGAGAGGGA | TGTGTCGATG | 540 |
| CACTCTGTTT | TCAAGGAGGA | GATTAGAGGG | ATCATGGGA | CGAAGCAGGT | GAAGATACCG | 600 |
| GCGGTTTTCG | TGAAGGGTAG | GATGATAGGA | AGCGTTGAGG | AAGTTGTGAG | GTTGGAGGAG | 660 |
| GAGGGTAAAT | TGGGTATTTT | GCTTGAGTGT | ATGCCTAAGG | CGAGGGTAAG | CGGTTGCTGC | 720 |
| TGCTGCGGGT | GCGGTGGGAT | GAGGTTTGTG | ATGTGTGGGG | TTTGTAATGG | AAGGCTGCAA | 780 |
| GGTTAGGGAT | GCGGAGAAGA | AGGATACGGT | TAAGTGTTTG | GAGTGTAATG | AGAATGGTTT | 840 |
| GGTTGTTTGT | CCAATGTGTT | CGTAAAGAG | GTTTCTTCTT | TTTCAGTTTT | GTCCTAATTT | 900 |
| TGTTGTGAAA | ATTGGGTGAG | ACTGTAAGAG | GGTTGACTTA | ACTTTGGAGG | CTAACTTTTT | 960 |
| GCATTTGAAT | CTTGATGGGT | AGAATCTAAT | GATTTGTGAG | AGAGTTTCTA | AAGTTGGGTT | 1020 |
| TAATGTTTCT | TGGTGTGTAC | TAGTAACTGA | ATCTGTGGTT | TAATGTTTGT | AAACGTTTTT | 1080 |
| ATAATAAAGA | TTCAATTTAT | TTTGTATAAC | CATCGTAAAT | ATCGTTTGT | TTGATTCTTT | 1140 |
| CTTCAATGTC | TACTATTTA | TTTTTGATA | AAATGTTAAT | TATCATGACA | AGTTTTGAT | 1200 |
| TTGTGACAGA | AATTACAAAA | ATAACTAGTA | GCAAAATGAT | GTAAATAAAC | TAAACACCAA | 1260 |
| TACTAACGGT | TATGAACTCA | GCCTGGTATA | ATAATCTTTC | TTCAATGGTC | TAATATGATT | 1320 |
| AACCACATAT | TCTTTCTTCA | TTGGTTCTAA | AGATGCTAAA | GTTTGGTTTG | ACTACTAACT | 1380 |
| AGTAATTGCA | ACTGCTTTTA | ATGTGTGTAA | GCGTTTTAT | ACATGATTCA | ATTTATTCTT | 1440 |
| CAGTGGTCTT | ATATGACAAA | CCACCTATTC | TTTCTTCATT | GAGTTTATTT | GCAATATGAA | 1500 |
| GCTAATAAAC | TTTTGTTTAT | AGTGATGATC | ATCAGATTAA | AAAATATAAC | GAATAAAGAA | 1560 |
| AAAATAGATA | AAAAAATTTG | AAAAAAAAAC | AAATAGATAA | ATTTTGAGAT | AATCATAACC | 1620 |
| GATATGATGA | CGAAAAGCAT | ACATAACTTG | GCACACATCC | CCAAATGATC | CCTGAATCTC | 1680 |
| AGGCACACAT | GTCAATGCAT | ATCCCCTATC | CATTTCCACC | TTTATAATTC | ATAACATCCG | 1740 |
| ACGATGATTT | TTATTCACAT | ATAACAAAAA | TAACAAAAGC | CAAAAAATG | | 1789 |

(2) INFORMATION FOR SEQ ID NO:2:

(i) SEQUENCE CHARACTERISTICS:
      (A) LENGTH: 2882 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

| | | | | | |
|---|---|---|---|---|---|
| TGTCCTTTAT | TGCTTTTCAG | TAGCATTCTA | ATTCAAAAAT | CATCTCACCC | ATTGATAGCA | 60 |
| TTTAGATTAA | GCATGGTCTT | ACATTCCCTT | TGCTTTAGAA | TCACTTAGAA | CTTATTTGAC | 120 |
| ATCTTTTATT | CTACAACATT | TGATTAAGAG | CCTTGAAACT | CCTATCATCA | TTCCTCAGAT | 180 |
| CGTTCATGAT | AATGCTTTGA | GTCCAGCCGT | TTCAGGATCA | CGTAAGAAGC | AAAAGACATC | 240 |
| ACAATCAATG | GCCTCATTAG | CGATGGGCCC | TCCATCTCCT | GCTATGCAAC | CATCTTCTTC | 300 |
| TGCGCTAAGA | AGGGGAGGTC | TTTCACCAGG | TATCTTATCT | TTCATTCCTA | CACAGTCAAG | 360 |
| TGACAATGTG | CTTTAGTGTC | TAGAGTTAAT | GGAGGTGTTG | TTGATGCAAT | TGCTTGGAT | 420 |
| CATAAGGTTT | TAATGCATAG | AATGAAAGAA | ATTAAGAACC | CCTAAATATG | AGACTCCCAT | 480 |
| TAGAGCACAA | AATCAAAGTG | TTTCTTAACT | AAAGTTCTTA | ATTACATTTA | AATACTAAAA | 540 |
| TAATCACTAA | GAGATCCTAA | GTGGGGTTGT | GGGTTAATCA | TGCTCTTATT | ATTCCAATTT | 600 |
| AAGAGGCTTT | TTTTTGTTTT | AATTGCTTTT | TTTCTTTTTT | TAATCATAAT | TTCATCTAAG | 660 |

| | | | | | | |
|---|---|---|---|---|---|---|
| AACCCCTTAA | GATACATGGA | TAATGATGCT | TTGAGAACAT | GATTATTGGA | AGGTTCTTAA | 720 |
| GGTGGGATTC | TTAGCGGAAT | ATAAGAATCT | GACTCTTAAT | TTTTAATTAA | AAAGACTAAG | 780 |
| AACCGGCTCT | TAAATAATAG | TTTTAAGAGA | CGGTTCTTAC | CTAGGAATCT | TTGCGATCAG | 840 |
| TCAATAGGCC | CATTGGGTCC | CAATCGTTGT | CTAAGTTGCC | TTTAAGTTTG | AAACCCATTG | 900 |
| ACCGATTTTT | ATTCTAGTTA | TTTTTTTGTC | CACCATTAAC | TCGTTCCTTC | ATGGCCCTAA | 960 |
| CTTTTGGTCG | CTGGATGACT | ATCTTTTTTC | TCTATGTTTC | ATATTGCTAG | TTGCATTGAT | 1020 |
| AAGATATTAT | CTTGAGCAGG | CAAGTAGACA | ACTGTTTTGA | TCCTCCAGAA | AAAAGTAAAG | 1080 |
| AAAAGGCAGC | AACACGAAAA | GATTATATAA | CAATTCCAAA | AGATAGATGC | CTAAAATAAA | 1140 |
| AGTCTATAAG | CACATCTATT | AATAAAATTT | CAAAGTAACT | GAAATGTATT | CGTAATCTCG | 1200 |
| TGAAGTATTT | GAACATGTAT | GTTATATTGA | TACATGTGTT | GGCTTGAGGT | TCATCGAATG | 1260 |
| GCTAAATCCG | AATGTGTTAT | TGAGCTAATA | TCATTGACAG | AGTTCTAATC | GTAAAAGCCC | 1320 |
| ATCCTGTGGC | ACACCTTCCA | ATGTGCAAGT | TGCAATATAA | AATCTGTTGT | CATTATATAA | 1380 |
| TTCGATTTTC | CCTTGAGAAA | ATAATTTATC | TGTTAATAGT | GACGTAGTCC | CCGCCGCGAC | 1440 |
| CAAGTAGCGT | CCTGATTTCA | TCAACGACCG | GTGATAAGTA | CTTAAATCGC | TCTAACATAT | 1500 |
| TACTTCCTCC | CATATAAGAT | ATATCCGATC | TGATGGTTAA | AATAATATTT | ATAAATTATA | 1560 |
| AGCAAAACAT | CATATTTATA | AATTATAAGC | AAAACATCCC | AGTTTTGTTA | CAAATACTCG | 1620 |
| AGTCTGGTTT | AAGTTAAGAT | CAGAATTCCC | GGTTTCTATT | TGTTTTTTTT | TTAATAAATT | 1680 |
| TTTTCAGTAA | CCCGTTTCCT | TTAAGTCAAG | TCAAACTGTA | TAATTAGTCC | TATTATTTTT | 1740 |
| ATAAGCAAAT | ACCAGAAAAT | GCCAACATCC | AAATTGGAAA | GATAGGATTG | CCAAGTCGCA | 1800 |
| TGCAATGTGC | AAATCCATTC | AAAGCAAGAT | AGGGTTTATC | TTTTTCCTC | GGGAAACATA | 1860 |
| ACTATTTGTT | TTGAAACTTT | TTTCCCACGT | TAAAGGTACG | ATTTTAAAAA | GTTACCCAT | 1920 |
| TTATACAATA | AGTACCAGTA | TTTTTTTTTG | GTAAAGAAA | AAGAACCCAA | ATAGCACTTA | 1980 |
| GAAAAATTTA | ATCGAATGAG | AATGTTTAGT | TCATATCTTC | AAACATCAAT | ATCGAATTTA | 2040 |
| TTGAGACCTA | GCAGCATGAA | TTAGCAATGG | CTAGTCCAGA | TAGTGCATGG | ATCTAAGAGA | 2100 |
| TTGAACTTGG | ATTTCACAAA | GATGTAATAT | AATGTGTTTT | ATACGAAAAA | GGAAGACTAA | 2160 |
| TATAACGTAA | GAAATTTTTG | TAAAATGTAG | ATCAGTTTTA | CCATAATGAG | AATGGTAAAA | 2220 |
| CTGATCTACA | TTTTGCAAGT | TTATTGATCA | AAAACGTGTG | AGGTTGGTAA | GACGACACGT | 2280 |
| TTGAAGCAAT | TGTGCATGTA | TAGAATTCTC | TGGAAGACTA | ATATAACGTA | AGAAATTTTT | 2340 |
| GTTCTTTGTT | AGTTAATTAA | TTACACCCAC | TTTGCCGACA | GATATACTCT | TTCCGATGAA | 2400 |
| GTTTGTGATT | ATTGCTTAAC | TGATTATTAG | ATCATATGGC | AACAAGATCT | TAGGCAATGC | 2460 |
| ATACTTACAT | GGACCAGCAC | ATATATCTGA | CCGTAACTGT | ATCCTAAATC | CTTGTGCAAC | 2520 |
| TCTGGTTCGC | ACTAAACTAT | ATACACTTCA | GATTTGTTTT | CTAGAATGAG | ATCAACAGAA | 2580 |
| AGAGACGATA | AAGGATGTCT | GATGATAATT | CGGTTCTGCC | ATAATTCACT | CGTACGTGTC | 2640 |
| ACAATTATTC | AAGTTTTGAG | AAAACAAAAA | TTTAAGCCAA | CTAGAGAAAG | ACATATACAC | 2700 |
| CAGCACAAGT | AACTTTTTCA | GTAAAATAGT | TTTAAATACT | TTATTTAAA | ATATTTTTT | 2760 |
| TAATTCAGAA | ACTAGTATAT | AAGGGGAAGA | AAGGAAAGAA | GAGCAACATG | CTTGAAGTTT | 2820 |
| CTCTACTTTC | ATAAGTCCTT | AAAAGAAAAA | TCATTTCCAA | TTCATAAAAT | TTGAAGCCAT | 2880 |
| GG | | | | | | 2882 |

( 2 ) INFORMATION FOR SEQ ID NO:3:

( i ) SEQUENCE CHARACTERISTICS:

( A ) LENGTH: 24 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:3:

GACGTTGTAA AACGACGGCC AGTG 24

( 2 ) INFORMATION FOR SEQ ID NO:4:

( i ) SEQUENCE CHARACTERISTICS:
              ( A ) LENGTH: 39 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:4:

TCAGAGCTCG GATCCGGTGG AAATGGATAG GGGATATGC 39

( 2 ) INFORMATION FOR SEQ ID NO:5:

( i ) SEQUENCE CHARACTERISTICS:
              ( A ) LENGTH: 11 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:5:

AAATAGATAA A 11

( 2 ) INFORMATION FOR SEQ ID NO:6:

( i ) SEQUENCE CHARACTERISTICS:
              ( A ) LENGTH: 10 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:6:

ATCTCAGGCA 10

( 2 ) INFORMATION FOR SEQ ID NO:7:

( i ) SEQUENCE CHARACTERISTICS:
              ( A ) LENGTH: 8 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:7:

CAATGCAT 8

( 2 ) INFORMATION FOR SEQ ID NO:8:

( i ) SEQUENCE CHARACTERISTICS:
              ( A ) LENGTH: 15 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:8:

CATGGATCCC AGCTC                                                                                15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TATGAGCTCG GATCC                                                                                15

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CATGGATCCG AGCTCATATC GGTTATGATT ATCTC                                                           35

( 2 ) INFORMATION FOR SEQ ID NO:11:

( i ) SEQUENCE CHARACTERISTICS:
        ( A ) LENGTH: 4 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GCTC                                                                                             4

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CATGGATCCG AGCTCTATGT ATGCTTTCG TCATC                                                            35

( 2 ) INFORMATION FOR SEQ ID NO:13:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GACTCCA                                                                                          7

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CTAGGATCCG AGCTCATCAT TTGGGGATGT GTGCC        35

( 2 ) INFORMATION FOR SEQ ID NO:15:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GAGCTCCACC GCGGTGGCGC CGTCTAGAAC TAGTGGATCC CCC        43

( 2 ) INFORMATION FOR SEQ ID NO:16:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

TATGAGCTCG GATCCATGTG TGCCTGAGAT TCAG        34

( 2 ) INFORMATION FOR SEQ ID NO:17:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GATCCGAGC        9

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

ACGAAAAGCA TACATAAC        18

( 2 ) INFORMATION FOR SEQ ID NO:19:

( i ) SEQUENCE CHARACTERISTICS:

( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

CAATGCATA                                                                                          9

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

ACGAAAAGCA TACATAAC                                                                                18

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

ACGAAAAGAT TATATAAC                                                                                18

( 2 ) INFORMATION FOR SEQ ID NO:22:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

GGCACACATC CCCAATG                                                                                 17

( 2 ) INFORMATION FOR SEQ ID NO:23:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

GGCACACATG TCAATG                                                                                  16

( 2 ) INFORMATION FOR SEQ ID NO:24:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (  i  i  ) MOLECULE TYPE: DNA (  x  i  ) SEQUENCE DESCRIPTION: SEQ ID NO:24:

GGCACACCTT CCAATG                                                                                          1 6

( 2 ) INFORMATION FOR SEQ ID NO:25:

(  i  ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear (  i  i  ) MOLECULE TYPE: DNA (  x  i  ) SEQUENCE DESCRIPTION: SEQ ID NO:25:

ATCTTAGGCA                                                                                                 1 0